United States Patent
Childs et al.

(10) Patent No.: US 11,779,603 B2
(45) Date of Patent: Oct. 10, 2023

(54) HERV-E REACTIVE T CELL RECEPTORS AND METHODS OF USE

(71) Applicants: The United States of America, as represented by the Secretary, Dept. of Health and Human Services, Bethesda, MD (US); Loyola University of Chicago, Maywood, IL (US)

(72) Inventors: Richard W. Childs, Rockville, MD (US); Michael I. Nishimura, Maywood, IL (US); Elena A. Cherkasova, Rockville, MD (US)

(73) Assignees: The United States of America, as represented by the Secretary, Department of Health and Human Services, Bethesda, MD (US); Loyola University of Chicago, Maywood, IL (US)

( * ) Notice: Subject to any disclaimer, the term of this patent is extended or adjusted under 35 U.S.C. 154(b) by 595 days.

(21) Appl. No.: 16/313,712

(22) PCT Filed: Jun. 30, 2017

(86) PCT No.: PCT/US2017/040448
§ 371 (c)(1),
(2) Date: Dec. 27, 2018

(87) PCT Pub. No.: WO2018/006054
PCT Pub. Date: Jan. 4, 2018

(65) Prior Publication Data
US 2019/0231821 A1    Aug. 1, 2019

Related U.S. Application Data

(60) Provisional application No. 62/357,265, filed on Jun. 30, 2016.

(51) Int. Cl.
| | |
|---|---|
| *A61K 35/17* | (2015.01) |
| *C07K 14/725* | (2006.01) |
| *C12N 15/85* | (2006.01) |
| *C07K 14/47* | (2006.01) |
| *C07K 14/005* | (2006.01) |

(52) U.S. Cl.
CPC .......... *A61K 35/17* (2013.01); *C07K 14/7051* (2013.01); *C12N 15/85* (2013.01); *C07K 14/005* (2013.01); *C07K 14/4748* (2013.01)

(58) Field of Classification Search
CPC ............................ A61K 35/17; C07K 14/7051
See application file for complete search history.

(56) References Cited

U.S. PATENT DOCUMENTS

| | | | |
|---|---|---|---|
| 2001/0039052 A1* | 11/2001 | Zander | C07K 14/70596 435/455 |
| 2013/0195819 A1 | 8/2013 | Wang et al. | |
| 2015/0152384 A1 | 6/2015 | Childs et al. | |

FOREIGN PATENT DOCUMENTS

| | | |
|---|---|---|
| CN | 101528926 A | 9/2009 |
| CN | 101557823 A | 10/2009 |
| CN | 102712636 A | 10/2012 |
| EP | 1224291 | 7/2002 |
| JP | 2013-176373 | 9/2013 |
| JP | 2013176373 A * | 9/2013 |
| WO | WO 2012/038055 A1 | 3/2012 |

OTHER PUBLICATIONS

Takahashi et al. Regression of human kidney cancer following allogeneic stem cell transplantation is associated with recognition of an HERV-E antigen by T cells(J Clin Invest. 2008; 118(3):1099-1109) (Year: 2008).*
Schaft et al. Peptide Fine Specificity of Anti-Glycoprotein 100 CTL Is Preserved Following Transfer of Engineered TCRGenes Into Primary Human T Lymphocytes (Journal of Immunology 2003; 170:2186-2194.) (Year: 2003).*
Roszkowski et al. CD8-Independent Tumor Cell Recognition Is a Property of the T Cell Receptor and Not the T Cell (The Journal of Immunology, 2003, 170: 2582-2589) (Year: 2003).*
Journal of Clinical Investigations. Author Information Center. 04032022 (Year: 2022).*
Cherkasova et al., "Endogenous retroviruses as targets for antitumor immunity in renal cell cancer and other tumors,"*Frontiers in Oncology*, 3:243, 2013 (5 pages).
Cherkasova et al., "Detection of an Immunogenic HERV-E Envelope with Selective Expression in Clear Cell Kidney Cancer," *Cancer Research*, vol. 76, No. 8, pp. 2177-2185, 2016.
Clay et al., "Potential Use of T Cell Receptor Genes to Modify Hematopoietic Stem Cells for the Gene Therapy of Cancer," *Pathology Oncology Research*, vol. 5, No. 1, pp. 3-15, 1999.
Debets et al., "TCR-engineered T cells to treat tumors: Seeing but not touching?" *Seminars in Immunobiology*, vol. 28, pp. 10-21, 2016.

(Continued)

*Primary Examiner* — Amy E Juedes
*Assistant Examiner* — Brian Hartnett
(74) *Attorney, Agent, or Firm* — Klarquist Sparkman, LLP

(57) ABSTRACT

Disclosed herein are T cell receptors (TCRs) capable of binding an antigen expressed by renal cell carcinoma cells. In some examples, the TCRs include an α chain (such as SEQ ID NO: 2) and a β chain (such as SEQ ID NO: 3). Also disclosed herein are vectors including nucleic acids encoding the disclosed TCR α and/or β chains. Further disclosed are modified T cells expressing the TCRs. In some examples, the modified T cells are prepared by transducing T cells with a vector including nucleic acids encoding the TCR α chain and the TCR β chain. In some embodiments, methods include treating a subject with RCC, by obtaining a population of T cells, transducing the population of T cells with a vector including a nucleic acids encoding the TCR α chain and the TCR β chain, and administering a composition comprising the modified T cells to the subject.

6 Claims, 10 Drawing Sheets

Specification includes a Sequence Listing.

(56) References Cited

OTHER PUBLICATIONS

Kirsch et al., "T-cell receptor profiling in cancer," *Molecular Oncology*, vol. 9, No. 10, pp. 2063-2070, 2015.
Norell et al., "CD34-Based Enrichment of Genetically-Engineered Human T Cells for Clinical Use Results in Dramatically Enhanced Tumor Targeting," *Cancer Immunol. Immunother*, vol. 59, No. 6, pp. 851-862, 2010 (Author Manuscript version, 22 pages).
Rooney et al., "Molecular and Genetic Properties of Tumors Associated with Local Immune Cytolytic Activity," *Cell*, vol. 160, pp. 48-61, 2015.
Rycaj et al., "Cytotoxicity of Human Endogenous Retrovirus K-Specific T Cells toward Autologous Ovarian Cancer Cells," *Clinical Cancer Research*, vol. 21, No. 2, pp. 471-483, 2014.
Schiavetti et al., "A Human Endogenous Retroviral Sequence Encoding an Antigen Recognized on Melanoma by Cytolytic T Lymphocytes," *Cancer Research*, vol. 62, No. 19, pp. 5510-5516, 2002.
Takahashi et al., "Regression of human kidney cancer following allogeneic stem cell transplantation is associated with recognition of an HERV-E antigen by T cells," *Journal of Clinical Investigation*, vol. 118, No. 3, pp. 1099-1109, 2008.

\* cited by examiner ccRCC cells | ccRCC + peptide

Donor 1 – grey columns
Donor 2 – black columns

Targets:

1 – ccRCC HERV-E neg/ HLA-A11+

2 – ccRCC HERV-E +/ HLA-A11+

3 – ccRCC HERV-E neg/ HLA-A11+
     + CT-RCC-1 peptide
4 – ccRCC HERV-E +/ HLA-A11+
     + CT-RCC-1 peptide

CD8+ T-cells

HERV-E Tetramer +

CD4+ T-cells

HERV-E Tetramer +

SEQUENCE LISTING

```
<160> NUMBER OF SEQ ID NOS: 7

<210> SEQ ID NO 1
<211> LENGTH: 10
<212> TYPE: PRT
<213> ORGANISM: Artificial Sequence
<220> FEATURE:
<223> OTHER INFORMATION: HERV-E peptide

<400> SEQUENCE: 1

Ala Thr Trp Leu Gly Ser Lys Thr Trp Lys
1               5                   10
```

-continued

```
<210> SEQ ID NO 2
<211> LENGTH: 807
<212> TYPE: DNA
<213> ORGANISM: Homo sapiens

<400> SEQUENCE: 2
atgaagagga tattgggagc tctgctgggg ctcttgagtg cccaggtttg ctgtgtgaga    60
ggaatacaag tggagcagag tcctccagac ctgattctcc aggagggagc caattccacg   120
ctgcggtgca atttttctga ctctgtgaac aatttgcagt ggtttcatca aaacccttgg   180
ggacagctca tcaacctgtt ttacattccc tcagggacaa acagaatgg aagattaagc    240 gccacgactg tcgctacgga acgctacagc ttattgtaca tttcctcttc ccagaccaca   300
gactcaggcg tttatttctg tgctgtgcga ggaggtgctg acggactcac ctttggcaaa   360
gggactcatc taatcatcca gcctatatc cagaaccctg accctgccgt gtaccagctg    420
agagactcta atccagtga caagtctgtc tgcctattca ccgattttga ttctcaaaca    480
aatgtgtcac aaagtaagga ttctgatgtg tatatcacag acaaaactgt gctagacatg   540
aggtctatgg acttcaagag caacagtgct gtggcctgga caacaaatc tgactttgca    600 tgtgcaaacg ccttcaacaa cagcattatt ccagaagaca ccttcttccc cagcccagaa   660
agttcctgtg atgtcaagct ggtcgagaaa agctttgaaa cagatacgaa cctaaacttt   720
caaaacctgt cagtgattgg gttccgaatc ctcctcctga agtggccgg gtttaatctg    780 ctcatgacgc tgcggctgtg gtccagc                                       807

<210> SEQ ID NO 3
<211> LENGTH: 921
<212> TYPE: DNA
<213> ORGANISM: Homo sapiens

<400> SEQUENCE: 3
atgggctgca ggctgctctg ctgtgcggtt ctctgtctcc tgggagcagt tcccatagac    60
actgaagtta cccagacacc aaaacacctg gtcatgggaa tgacaaataa gaagtctttg   120
aaatgtgaac aacatatggg gcacagggct atgtattggt acaagcagaa agctaagaag   180
ccaccggagc tcatgtttgt ctacagctat gagaaactct ctataaatga agtgtgcca    240 agtcgcttct cacctgaatg ccccaacagc tctctcttaa accttcacct acacgccctg   300
cagccagaag actcagccct gtatctctgc gccagcagcc ctcccaatga aaactgtttt   360
tttggcagtg gaacccagct ctctgtcttg gaggacctga caaggtgttt cccacccgag   420
gtcgctgtgt ttgagccatc agaagcagag atctcccaca cccaaaaggc cacactggtg   480
tgcctggcca caggcttctt ccctgaccac gtggagctga gctggtgggt gaatgggaag   540
gaggtgcaca gtggggtcag cacggacccg cagcccctca aggagcagcc cgccctcaat   600
gactccagat actgcctgag cagccgcctg agggtctcgg ccaccttctg gcagaacccc   660
cgcaaccact ccgctgtca agtccagttc tacgggctct cggagaatga cgagtggacc   720
caggataggg ccaaacccgt cacccagatc gtcagcgccg aggcctgggg tagagcagac   780
tgtggcttta cctcggtgtc ctaccagcaa ggggtcctgt ctgccaccat cctctatgag   840
atcctgctag gaaggccac cctgtatgct gtgctggtca gcgcccttgt gttgatggca   900
atggtcaaga gaaaggattt c                                            921

<210> SEQ ID NO 4
<211> LENGTH: 269
<212> TYPE: PRT
```

<213> ORGANISM: Homo sapiens

<400> SEQUENCE: 4

```
Met Lys Arg Ile Leu Gly Ala Leu Leu Gly Leu Leu Ser Ala Gln Val
1               5                   10                  15
Cys Cys Val Arg Gly Ile Gln Val Glu Gln Ser Pro Pro Asp Leu Ile
            20                  25                  30
Leu Gln Glu Gly Ala Asn Ser Thr Leu Arg Cys Asn Phe Ser Asp Ser
        35                  40                  45
Val Asn Asn Leu Gln Trp Phe His Gln Asn Pro Trp Gly Gln Leu Ile
50                  55                  60
Asn Leu Phe Tyr Ile Pro Ser Gly Thr Lys Gln Asn Gly Arg Leu Ser
65                  70                  75                  80
Ala Thr Thr Val Ala Thr Glu Arg Tyr Ser Leu Leu Tyr Ile Ser Ser
                85                  90                  95
Ser Gln Thr Thr Asp Ser Gly Val Tyr Phe Cys Ala Val Arg Gly Gly
            100                 105                 110
Ala Asp Gly Leu Thr Phe Gly Lys Gly Thr His Leu Ile Ile Gln Pro
        115                 120                 125
Tyr Ile Gln Asn Pro Asp Pro Ala Val Tyr Gln Leu Arg Asp Ser Lys
130                 135                 140
Ser Ser Asp Lys Ser Val Cys Leu Phe Thr Asp Phe Asp Ser Gln Thr
145                 150                 155                 160
Asn Val Ser Gln Ser Lys Asp Ser Asp Val Tyr Ile Thr Asp Lys Thr
                165                 170                 175
Val Leu Asp Met Arg Ser Met Asp Phe Lys Ser Asn Ser Ala Val Ala
            180                 185                 190
Trp Ser Asn Lys Ser Asp Phe Ala Cys Ala Asn Ala Phe Asn Asn Ser
        195                 200                 205
Ile Ile Pro Glu Asp Thr Phe Phe Pro Ser Pro Glu Ser Ser Cys Asp
210                 215                 220
Val Lys Leu Val Glu Lys Ser Phe Glu Thr Asp Thr Asn Leu Asn Phe
225                 230                 235                 240
Gln Asn Leu Ser Val Ile Gly Phe Arg Ile Leu Leu Leu Lys Val Ala
                245                 250                 255
Gly Phe Asn Leu Leu Met Thr Leu Arg Leu Trp Ser Ser
            260                 265
```

<210> SEQ ID NO 5
<211> LENGTH: 307
<212> TYPE: PRT
<213> ORGANISM: Homo sapiens

<400> SEQUENCE: 5

```
Met Gly Cys Arg Leu Leu Cys Cys Ala Val Leu Cys Leu Leu Gly Ala
1               5                   10                  15
Val Pro Ile Asp Thr Glu Val Thr Gln Thr Pro Lys His Leu Val Met
            20                  25                  30
Gly Met Thr Asn Lys Lys Ser Leu Lys Cys Glu Gln His Met Gly His
        35                  40                  45
Arg Ala Met Tyr Trp Tyr Lys Gln Lys Ala Lys Lys Pro Pro Glu Leu
        50                  55                  60
Met Phe Val Tyr Ser Tyr Glu Lys Leu Ser Ile Asn Glu Ser Val Pro
65                  70                  75                  80
Ser Arg Phe Ser Pro Glu Cys Pro Asn Ser Ser Leu Leu Asn Leu His
```

```
                    85                  90                  95
Leu His Ala Leu Gln Pro Glu Asp Ser Ala Leu Tyr Leu Cys Ala Ser
                100                 105                 110

Ser Pro Pro Asn Glu Lys Leu Phe Phe Gly Ser Gly Thr Gln Leu Ser
                115                 120                 125

Val Leu Glu Asp Leu Asn Lys Val Phe Pro Pro Glu Val Ala Val Phe
            130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
                180                 185                 190

Leu Lys Glu Gln Pro Ala Leu Asn Asp Ser Arg Tyr Cys Leu Ser Ser
                195                 200                 205

Arg Leu Arg Val Ser Ala Thr Phe Trp Gln Asn Pro Arg Asn His Phe
            210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
                260                 265                 270

Leu Ser Ala Thr Ile Leu Tyr Glu Ile Leu Leu Gly Lys Ala Thr Leu
            275                 280                 285

Tyr Ala Val Leu Val Ser Ala Leu Val Leu Met Ala Met Val Lys Arg
        290                 295                 300

Lys Asp Phe
305

<210> SEQ ID NO 6
<211> LENGTH: 7948
<212> TYPE: DNA
<213> ORGANISM: Artificial Sequence
<220> FEATURE:
<223> OTHER INFORMATION: Recombinant retroviral vector

<400> SEQUENCE: 6
aggcgtatca cgaggccctt tcgtcttcaa gaattcatac cagatcaccg aaaactgtcc     60
tccaaatgtg tccccctcac actcccaaat tcgcgggctt ctgcctctta gaccactcta    120
ccctattccc cacactcacc ggagccaaag ccgcggagcg cgttgacatt gattattgac    180
tagttattaa tagtaatcaa ttacggggtc attagttcat agcccatata tggagttccg    240
cgttacataa cttacggtaa atggcccgcc tggctgaccg cccaacgacc cccgcccatt    300
gacgtcaata atgacgtatg ttcccatagt aacgccaata gggactttcc attgacgtca    360
atgggtggag tatttacggt aaactgccca cttggcagta catcaagtgt atcatatgcc    420
aagtacgccc cctattgacg tcaatgacgg taaatggccc gcctggcatt atgcccagta    480
catgacctta tgggactttc ctacttggca gtacatctac gtattagtca tcgctattac    540
catggtgatg cggttttggc agtacatcaa tgggcgtgga tagcggtttg actcacgggg    600
atttccaagt ctccacccca ttgacgtcaa tgggagtttg ttttggcacc aaaatcaacg    660
ggactttcca aaatgtcgta caactccgcc ccattgacg caaatgggcg gtaggcgtgt    720
acggtgggag gtctatataa gcagagctca ataaaagagc ccacaacccc tcactcggcg    780
```

```
cgccagtctt ccgatagact gcgtcgcccg ggtacccgta ttcccaataa agcctcttgc    840
tgtttgcatc cgaatcgtgg tctcgctgtt ccttgggagg gtctcctctg agtgattgac    900
tacccacgac gggggtcttt catttggggg ctcgtccggg atttggagac ccctgcccag    960
ggaccaccga cccaccaccg ggaggtaagc tggccagcaa cttatctgtg tctgtccgat   1020
tgtctagtgt ctatgtttga tgttatgcgc ctgcgtctgt actagttagc taactagctc   1080
tgtatctggc ggaccgtgg tggaactgac gagttctgaa cacccggccg caaccctggg    1140
agacgtccca gggactttgg gggccgtttt tgtggcccga cctgaggaag ggagtcgatg   1200
tggaatccga ccccgtcagg atatgtggtt ctggtaggag acgagaacct aaaacagttc   1260
ccgcctccgt ctgaattttt gctttcggtt tggaaccgaa gccgcgcgtc ttgtctgctg   1320
cagcgctgca gcatcgttct gtgttgtctc tgtctgactg tgtttctgta tttgtctgaa   1380
aattagggcc agactgttac cactccctta agtttgacct taggtcactg gaaagatgtc   1440
gagcggatcg ctcacaacca gtcggtagat gtcaagaaga gacgttgggt taccttctgc   1500
tctgcagaat ggccaacctt taacgtcgga tggccgcgag acggcacctt taaccgagac   1560
ctcatcaccc aggttaagat caaggtcttt tcacctggcc cgcatggaca cccagaccag   1620
gtcccctaca tcgtgacctg ggaagccttg gcttttgacc ccctccctg ggtcaagccc    1680 tttgtacacc ctaagcctcc gcctcctctt cctccatccg ccccgtctct cccccttgaa   1740
cctcctcgtt cgaccccgcc tcgatcctcc ctttatccag ccctcactcc ttctctaggc   1800
gccggaattc gcggccgtga caagagttac taacagcccc tctctccaag ctcacttaca   1860
ggctctctac ttagtccagc acgaagtctg agacctctg gcggcagcct accaagaaca    1920
actggaccga ccggtggtac ctcaccctta ccgagtcggc gacacagtgt gggtccgccg   1980
acaccagact aagaacctag aacctcgctg gaaaggacct tacacagtcc tgctgaccac   2040
ccccaccgcc ctcaaagtag acggcatcgc agcttggata cacgccgccc acgtgaaggc   2100
tgccgacccc gggggtggac catcctctag actgacgcgg ccgcgagcaa gaaggcaaag   2160
catcatgaag aggatattgg gagctctgct ggggctcttg agtgcccagg tttgctgtgt   2220
gagaggaata caagtggagc agagtcctcc agacctgatt ctccaggagg gagccaattc   2280
cacgctgcgg tgcaattttt ctgactctgt gaacaatttg cagtggtttc atcaaaaccc   2340
ttggggacag ctcatcaacc tgttttacat tccctcaggg acaaaacaga atggaagatt   2400
aagcgccacg actgtcgcta cggaacgcta cagcttattg tacatttcct cttcccagac   2460
cacagactca ggcgtttatt tctgtgctgt gcgaggaggt gctgacggac tcacctttgg   2520
caaagggact catctaatca tccagcccta tatccagaac cctgaccctg ccgtgtacca   2580
gctgagagac tctaaatcca gtgacaagtc tgtctgccta ttcaccgatt ttgattctca   2640
aacaaatgtg tcacaaagta aggattctga tgtgtatatc acagacaaaa ctgtgctaga   2700
catgaggtct atggacttca gagcaacag tgctgtggcc tggagcaaca atctgactt     2760 tgcatgtgca aacgccttca caacagcat tattccagaa gacaccttct tccccagccc    2820
agaaagttcc tgtgatgtca agctggtcga gaaaagcttt gaaacagata cgaacctaaa   2880
ctttcaaaac ctgtcagtga ttgggttccg aatcctcctc ctgaaagtgg ccgggtttaa   2940
tctgctcatg acgctgcggc tgtggtccag cgggtccgga gccacgaact tctctctgtt   3000
aaagcaagca ggagacgtgg aggagaaccc cggtcctatg gctgcaggc tgctctgctg    3060 tgcggttctc tgtctcctgg gagcagttcc catagacact gaagttaccc agacaccaaa   3120
```

```
acacctggtc atggaatga caaataagaa gtctttgaaa tgtgaacaac atatggggca    3180
cagggctatg tattggtaca agcagaaagc taagaagcca ccggagctca tgtttgtcta    3240
cagctatgag aaactctcta taaatgaaag tgtgccaagt cgcttctcac ctgaatgccc    3300
caacagctct ctcttaaacc ttcacctaca cgccctgcag ccagaagact cagccctgta    3360
tctctgcgcc agcagccctc ccaatgaaaa actgtttttt ggcagtggaa cccagctctc    3420
tgtcttggag gacctgaaca aggtgttccc acccgaggtc gctgtgtttg agccatcaga    3480
agcagagatc tcccacaccc aaaaggccac actggtgtgc ctggccacag gcttcttccc    3540
tgaccacgtg gagctgagct ggtgggtgaa tgggaaggag gtgcacagtg gggtcagcac    3600
ggacccgcag cccctcaagg agcagcccgc cctcaatgac tccagatact gcctgagcag    3660
ccgcctgagg gtctcggcca ccttctggca gaaccccgc aaccacttcc gctgtcaagt    3720
ccagttctac gggctctcgg agaatgacga gtggaccccag gatagggcca aacccgtcac    3780
ccagatcgtc agcgccgagg cctggggtag agcagactgt ggctttacct cggtgtccta    3840
ccagcaaggg gtcctgtctg ccaccatcct ctatgagatc ctgctaggga aggccaccct    3900
gtatgctgtg ctggtcagcg cccttgtgtt gatggcaatg gtcaagagaa aggatttcga    3960
attcggctca ggcgagggca gaggcagtct gctaacatgc ggtgatgtcg aagaaaatcc    4020
tggcccaccg cggggctgga ccgcgctttg cttgctgagt ttgctgcctt ctgggttcat    4080
gagtcttgac aacaacggta ctgctacccc agagttacct acccagggaa cattttcaaa    4140
tgtttctaca aatgtatcct accaagaaac tacaacacct agtacccttg aagtaccag    4200
cctgcaccct gtgtctcaac atggcaatga ggccacaaca aacatcacag aaacgacagt    4260
caaattcaca tctacctctg tgataacctc agtttatgga aacacaaact cttctgtcca    4320
gtcacagacc tctgtaatca gcacagtgtt caccacccca gccaacgttt caactccaga    4380
gacaaccttg aagcctagcc tgtcacctgg aaatgtttca gacctttcaa ccactagcac    4440
tagccttgca acatctccca ctaaaccta tacatcatct tctcctatcc taagtgacat    4500
caaggcagaa atcaaatgtt caggcatcag agaagtgaaa ttgactcagg gcatctgcct    4560
ggagcaaaat aagacctcca gctgtgcgga gtttaagaag gacagggag agggcctggc    4620
ccgagtgctg tgtggggagg agcaggctga tgctgatgct ggggcccagg tatgctccct    4680
gctccttgcc cagtctgagg tgagacctca gtgtctactg ctggtcttgg ccaacagaac    4740
agaaatttcc agcaaactcc aacttatgaa aaagcaccaa tctgacctga aaagctggg    4800
catcctagat ttcactgagc aagatgttgc aagccaccag agctattccc aaaagaccct    4860
gattgcactg gtcacctcgg agccctgct ggctgtcttg ggcatcactg gctatttcct    4920
gatgaatcgc cgcagctgga gcccacagg agaaaggctg gaactagaac catgaggatc    4980
cgataaaata aaagatttta tttagtctcc agaaaaaggg gggaatgaaa gaccccacct    5040
gtaggtttgg caagctagct taagtaacgc catttttgcaa ggcatggaaa atacataaac    5100
tgagaataga gaagttcaga tcaaggtcag gaacagatgg aacagctgaa tatgggccaa    5160
acaggatatc tgtggtaagc agttcctgcc ccggctcagg gccaagaaca gatggaacag    5220
ctgaatatgg gccaaacagg atatctgtgg taagcagttc ctgccccggc tcagggccaa    5280
gaacagatgg tccccagatg cggtccagcc ctcagcagtt tctagagaac catcagatgt    5340
ttccagggtg ccccaaggac ctgaaatgac cctgtgcctt atttgaacta accaatcagt    5400
tcgcttctcg cttctgttcg cgcgcttctg ctccccgagc tcaataaaag agcccacaac    5460
ccctcactcg gggcgccagt cctccgattg actgagtcgc ccgggtaccc gtgtatccaa    5520
```

```
taaaccctct tgcagttgca tccgacttgt ggtctcgctg ttccttggga gggtctcctc  5580
tgagtgattg actacccgtc agcggggtc tttcatttgg gggctcgtcc gggatcggga   5640
gaccctgcc cagggaccac cgacccacca ccgggaggta agctggctgc ctcgcgcgtt   5700
tcggtgatga cggtgaaaac ctctgacaca tgcagctccc ggagacggtc acagcttgtc  5760
tgtaagcgga tgccgggagc agacaagccc gtcagggcgc gtcagcgggt gttggcgggt  5820
gtcggggcgc agccatgacc cagtcacgta gcgatagcgg agtgtatact ggcttaacta  5880
tgcggcatca gagcagattg tactgagagt gcaccatatg cggtgtgaaa taccgcacag  5940
atgcgtaagg agaaaatacc gcatcaggcg ctcttccgct tcctcgctca ctgactcgct  6000
gcgctcggtc gttcggctgc ggcgagcggt atcagctcac tcaaaggcgg taatacggtt  6060
atccacagaa tcaggggata acgcaggaaa gaacatgtga gcaaaaggcc agcaaaaggc  6120
caggaaccgt aaaaaggccg cgttgctggc gttttccat aggctccgcc cccctgacga   6180
gcatcacaaa aatcgacgct caagtcagag gtggcgaaac ccgacaggac tataaagata  6240
ccaggcgttt ccccctggaa gctccctcgt gcgctctcct gttccgaccc tgccgcttac  6300
cggatacctg tccgcctttc tcccttcggg aagcgtggcg ctttctcata gctcacgctg  6360
taggtatctc agttcggtgt aggtcgttcg ctccaagctg ggctgtgtgc acgaaccccc  6420
cgttcagccc gaccgctgcg ccttatccgg taactatcgt cttgagtcca acccggtaag  6480
acacgactta tcgccactgg cagcagccac tggtaacagg attagcagag cgaggtatgt  6540
aggcggtgct acagagttct tgaagtggtg gcctaactac ggctacacta aaggacagt   6600
atttggtatc tgcgctctgc tgaagccagt taccttcgga aaaagagttg gtagctcttg  6660
atccggcaaa caaccaccg ctggtagcgg tggtttttt gtttgcaagc agcagattac    6720
gcgcagaaaa aaggatctc aagaagatcc tttgatcttt tctacggggt ctgacgctca   6780
gtggaacgaa aactcacgtt aagggatttt ggtcatgaga ttatcaaaaa ggatcttcac  6840
ctagatcctt ttaaattaaa aatgaagttt taaatcaatc taaagtatat atgagtaaac  6900
ttggtctgac agttaccaat gcttaatcag tgaggcacct atctcagcga tctgtctatt  6960
tcgttcatcc atagttgcct gactccccgt cgtgtagata actacgatac gggagggctt  7020
accatctggc cccagtgctg caatgatacc gcgagaccca cgctcaccgg ctccagattt  7080
atcagcaata aaccagccag ccggaagggc cgagcgcaga agtggtcctg caactttatc  7140
cgcctccatc cagtctatta attgttgccg ggaagctaga gtaagtagtt cgccagttaa  7200
tagtttgcgc aacgttgttg ccattgctgc aggcatcgtg gtgtcacgct cgtcgtttgg  7260
tatggcttca ttcagctccg gttcccaacg atcaaggcga gttacatgat cccccatgtt  7320
gtgcaaaaaa gcggttagct ccttcggtcc tccgatcgtt gtcagaagta agttggccgc  7380
agtgttatca ctcatggtta tggcagcact gcataattct cttactgtca tgccatccgt  7440
aagatgcttt tctgtgactg gtgagtactc aaccaagtca ttctgagaat agtgtatgcg  7500
gcgaccgagt tgctcttgcc cggcgtcaac acgggataat accgcgccac atagcagaac  7560
tttaaaagtg ctcatcattg gaaaacgttc ttcgggcga aaactctcaa ggatcttacc   7620
gctgttgaga tccagttcga tgtaacccac tcgtgcaccc aactgatctt cagcatcttt  7680
tactttcacc agcgtttctg ggtgagcaaa aacaggaagg caaaatgccg caaaaaaggg  7740
aataagggcg acacggaaat gttgaatact catactcttc cttttcaat attattgaag   7800
catttatcag ggttattgtc tcatgagcgg atacatattt gaatgtattt agaaaaataa  7860
```

-continued

```
acaaataggg gttccgcgca catttccccg aaaagtgcca cctgacgtct aagaaaccat      7920
tattatcatg acattaacct ataaaaat                                         7948
```

```
<210> SEQ ID NO 7
<211> LENGTH: 315
<212> TYPE: PRT
<213> ORGANISM: Artificial Sequence
<220> FEATURE:
<223> OTHER INFORMATION: Truncated CD34 polypeptide

<400> SEQUENCE: 7

Pro Arg Gly Trp Thr Ala Leu Cys Leu Leu Ser Leu Leu Pro Ser Gly
1               5                   10                  15

Phe Met Ser Leu Asp Asn Asn Gly Thr Ala Thr Pro Glu Leu Pro Thr
            20                  25                  30

Gln Gly Thr Phe Ser Asn Val Ser Thr Asn Val Ser Tyr Gln Glu Thr
        35                  40                  45

Thr Thr Pro Ser Thr Leu Gly Ser Thr Ser Leu His Pro Val Ser Gln
    50                  55                  60

His Gly Asn Glu Ala Thr Thr Asn Ile Thr Glu Thr Thr Val Lys Phe
65                  70                  75                  80

Thr Ser Thr Ser Val Ile Thr Ser Val Tyr Gly Asn Thr Asn Ser Ser
                85                  90                  95

Val Gln Ser Gln Thr Ser Val Ile Ser Thr Val Phe Thr Thr Pro Ala
            100                 105                 110

Asn Val Ser Thr Pro Glu Thr Thr Leu Lys Pro Ser Leu Ser Pro Gly
        115                 120                 125

Asn Val Ser Asp Leu Ser Thr Thr Ser Thr Ser Leu Ala Thr Ser Pro
    130                 135                 140

Thr Lys Pro Tyr Thr Ser Ser Ser Pro Ile Leu Ser Asp Ile Lys Ala
145                 150                 155                 160

Glu Ile Lys Cys Ser Gly Ile Arg Glu Val Lys Leu Thr Gln Gly Ile
                165                 170                 175

Cys Leu Glu Gln Asn Lys Thr Ser Ser Cys Ala Glu Phe Lys Lys Asp
            180                 185                 190

Arg Gly Glu Gly Leu Ala Arg Val Leu Cys Gly Glu Glu Gln Ala Asp
        195                 200                 205

Ala Asp Ala Gly Ala Gln Val Cys Ser Leu Leu Leu Ala Gln Ser Glu
    210                 215                 220

Val Arg Pro Gln Cys Leu Leu Leu Val Leu Ala Asn Arg Thr Glu Ile
225                 230                 235                 240

Ser Ser Lys Leu Gln Leu Met Lys Lys His Gln Ser Asp Leu Lys Lys
                245                 250                 255

Leu Gly Ile Leu Asp Phe Thr Glu Gln Asp Val Ala Ser His Gln Ser
            260                 265                 270

Tyr Ser Gln Lys Thr Leu Ile Ala Leu Val Thr Ser Gly Ala Leu Leu
        275                 280                 285

Ala Val Leu Gly Ile Thr Gly Tyr Phe Leu Met Asn Arg Arg Ser Trp
    290                 295                 300

Ser Pro Thr Gly Glu Arg Leu Glu Leu Glu Pro
305                 310                 315
```

HERV-E REACTIVE T CELL RECEPTORS AND METHODS OF USE

CROSS REFERENCE TO RELATED APPLICATIONS

This application is the § 371 U.S. National Stage of International Application No. PCT/US2017/040448, filed Jun. 30, 2017, which was published in English under PCT Article 21(2), which in turn claims the benefit of U.S. Provisional Application No. 62/357,265, filed Jun. 30, 2016, which is herein incorporated by reference in its entirety.

FIELD

This disclosure relates to cancer immunotherapy, particularly T cells expressing a renal cell carcinoma-reactive T cell receptor, and methods of making and using the T cells.

BACKGROUND

Renal cell carcinoma (RCC) is responsible for approximately 12,000 deaths every year in the United States alone. As with most cancer, when detected at early stages, surgical intervention is highly effective. Despite progress in treating RCC with targeted inhibitors and inhibitors of immune checkpoints (such as anti-CTLA-4 and anti-PD-1 monoclonal antibodies), metastatic RCC is generally lethal, with mean survival being less than a year. Thus, there remains a need for more effective therapies for RCC.

SUMMARY

Disclosed herein are T cell receptors (TCRs) recognizing an antigen expressed on RCC cells. T cells can be transduced with a nucleic acid encoding the TCR (e.g., TCR α and β chains) and administered to a subject with RCC in order to treat or inhibit RCC in the subject.

Disclosed herein are TCRs that are capable of binding a human endogenous retrovirus-E (HERV-E) antigen expressed by RCC cells (e.g., a peptide having the sequence ATWLGSKTWK; SEQ ID NO: 1). In some examples, the TCRs are HLA-A11 restricted TCRs expressed by clear cell renal cell carcinoma (ccRCC) cells. In some examples, the TCRs include an α chain (such as an α chain having an amino acid sequence with at least 95% sequence identity to SEQ ID NO: 4) and a β chain (such as a β chain having an amino acid sequence with at least 95% sequence identity to SEQ ID NO: 5). In some examples, the TCR α chain is encoded by a nucleic acid having at least 90% sequence identity to SEQ ID NO: 2 and the TCR β chain is encoded by a nucleic acid having at least 90% sequence identity to SEQ ID NO: 3.

Also disclosed herein are vectors (such as viral vectors) including nucleic acids encoding the disclosed TCR α and/or β chains, for example, operably linked to an expression control sequence (such as a promoter). In some examples, the vector also includes a nucleic acid encoding a truncated CD34 protein, such as a CD34 protein including the extracellular and transmembrane domains, but lacking the intracellular domain. In one non-limiting example, the vector is a retroviral vector (such as a SAMEN vector) including nucleic acids encoding the TCR α chain (such as SEQ ID NO: 2), the TCR β chain (such as SEQ ID NO: 3), and the truncated CD34.

Further disclosed are modified T cells expressing the TCRs capable of binding the HERV-E antigen expressed by RCC cells (such as ccRCC cells), such as nucleic acids encoding the TCR α chain (for example, SEQ ID NO: 2) and the TCR β chain (for example, SEQ ID NO: 3). In some examples, the modified T cells are prepared by transducing T cells (such as T cells obtained from a subject with RCC or a donor) with a vector including nucleic acids encoding the TCR α chain and the TCR β chain, and optionally the truncated CD34 protein.

In some embodiments, methods include treating a subject with RCC (for example, ccRCC or metastatic ccRCC), by obtaining a population of T cells from the subject or a donor, transducing the population of T cells with vector including a nucleic acids encoding the TCR α chain (such as SEQ ID NO: 2) and the TCR β chain (such as SEQ ID NO: 3), producing a population of modified T cells, and administering a composition including the modified T cells to the subject. In some examples, the population of T cells is activated in vitro prior to transduction with the nucleic acid molecule. In other examples, the population of modified T cells is expanded and/or enriched prior to administering to the subject.

The foregoing and other features of the disclosure will become more apparent from the following detailed description, which proceeds with reference to the accompanying figures.

SEQUENCE LISTING

Figure 1:
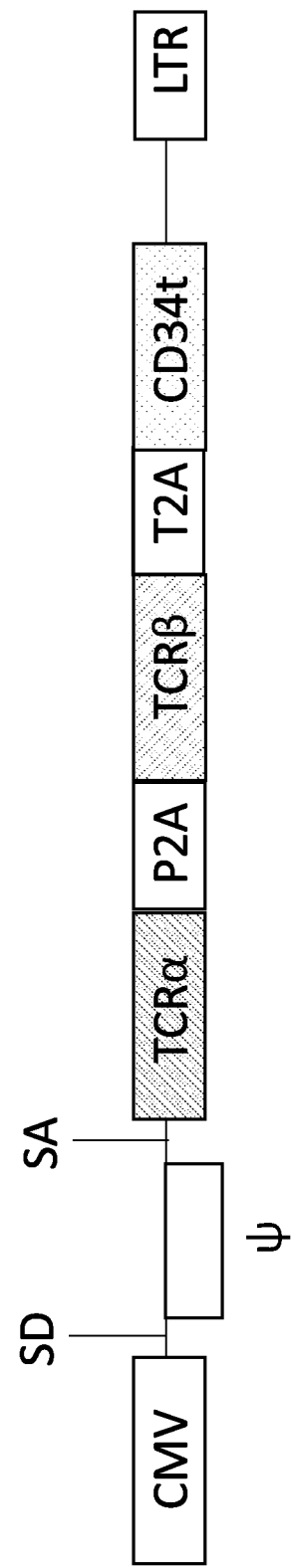
FIG. 1 is a schematic diagram of an exemplary retroviral vector for expression of the TCR α and β chains described herein. CMV, human cytomegalovirus promoter/enhancer; ψ, packaging signal; SD, splice donor; SA, splice acceptor; TCRα, HERV-E antigen specific TCR α chain (e.g., SEQ ID NO: 2); P2A, self-cleaving 2A peptide derived from porcine teschovirus; TCRβ, HERV-E antigen specific TCR β chain (e.g., SEQ ID NO: 3); T2A, self-cleaving 2A peptide of *Thosea asigna* virus; CD34t, truncated CD34 with extracellular and transmembrane regions of the protein; LTR, 3' LTR.
Figure 2:
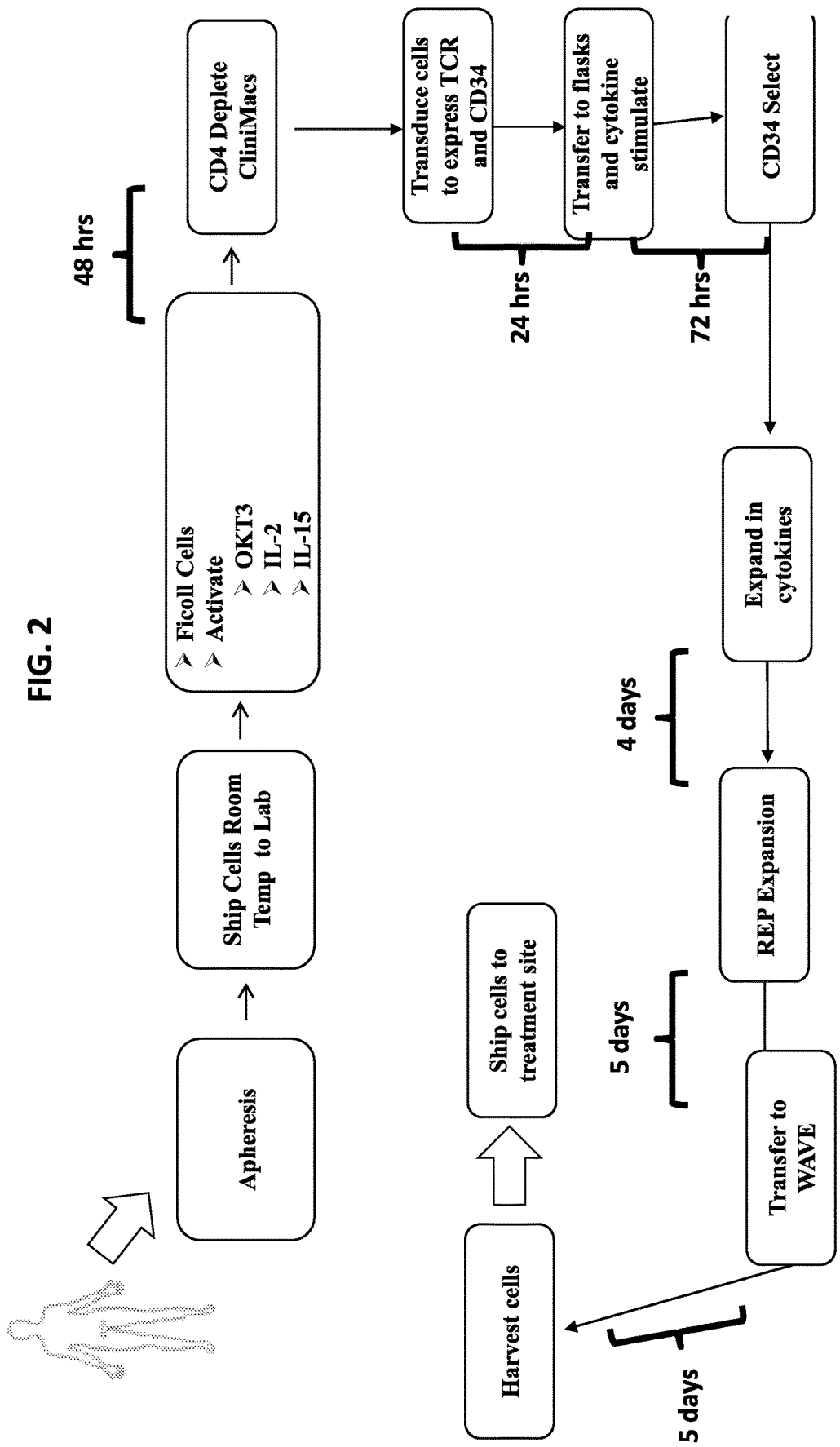
FIG. 2 is a schematic diagram of an exemplary protocol for collecting and producing modified T cells for treating a subject with RCC

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Dec. 27, 2018, and is ~21 kilobytes, which is incorporated by reference herein.

SEQ ID NO: 1 is the amino acid sequence of an HLA-A11 RCC-specific HERV-E antigenic peptide.

SEQ ID NO: 2 is the nucleic acid sequence of an exemplary RCC HERV-reactive TCR alpha chain.

SEQ ID NO: 3 is the nucleic acid sequence of an exemplary RCC HERV-reactive beta chain.

SEQ ID NO: 4 is the amino acid sequence of an exemplary RCC HERV-reactive TCR alpha chain.

SEQ ID NO: 5 is the amino acid sequence of an exemplary RCC HERV-reactive beta chain.

SEQ ID NO: 6 is the nucleic acid sequence of an exemplary SAMEN vector for expression of the RCC HERV-reactive TCR and truncated CD34.

SEQ ID NO: 7 is the amino acid sequence of an exemplary truncated CD34 (CD34t) protein.

DETAILED DESCRIPTION

An allogeneic T cell clone was previously isolated from a RCC patient who showed prolonged tumor regression after an allogeneic transplant (Takahashi et al., *J. Clin. Invest.* 118:1099-1109, 2008). This HLA-A11 restricted CD8+ T cell clone was highly cytotoxic to ccRCC cell lines that were HLA-A11 positive, but did not kill non-malignant cells (Takahashi et al., 2008). Using cDNA expression cloning, the antigen recognized by this clone, which is encoded by an endogenous retrovirus type E (HERV-E), was identified (Takahashi et al., 2008). This antigen was expressed in ccRCC but not observed in normal tissues or other tumor types and is expressed by about 80% of ccRCC tumors.

The present inventors have identified the T cell receptor expressed by the T cell clone isolated from the RCC patient. As described herein, this TCR can be used for gene transfer immunotherapy for treating RCC patients. T cells are transduced with genes encoding the TCR α and β chains and are administered to a subject with RCC to redirect specificity of normal T cells from the subject to the RCC cells.

I. Abbreviations ccRCC clear cell renal cell carcinoma
CD34t truncated CD34
CTL cytotoxic T lymphocyte
HERV human endogenous retrovirus
HLA human leukocyte antigen
LTR: long terminal repeat
MMLV Moloney murine leukemia virus
PBMC peripheral blood mononuclear cells
RCC renal cell carcinoma
TCR T cell receptor II. Terms Unless otherwise noted, technical terms are used according to conventional usage.

Definitions of common terms in molecular biology may be found in *Lewin's Genes X*, ed. Krebs et al., Jones and Bartlett Publishers, 2009 (ISBN 0763766321); Kendrew et al. (eds.), The *Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics*, 3rd Edition, Springer, 2008 (ISBN: 1402067534); and other similar references.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of the present disclosure, suitable methods and materials are described below. All publications, patent applications, patents, and other references mentioned herein are incorporated by reference in their entirety. Sequences associated with GenBank Accession Numbers are herein incorporated by reference as present in GenBank on Jun. 30, 2016, unless otherwise noted. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Antigen: A compound, composition, or substance that can stimulate the production of antibodies or a T cell response in a subject. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, about 7-11, or about 8-10 amino acids in a unique spatial conformation. Methods of determining spatial conformation of epitopes include, for example, x-ray crystallography and two-dimensional nuclear magnetic resonance.

An antigen can be a tissue-specific antigen, or a disease-specific antigen. These terms are not exclusive, as a tissue-specific antigen can also be a disease-specific antigen. A tissue-specific antigen is expressed in a limited number of tissues, such as a single tissue. A disease-specific antigen is expressed coincidentally with a disease process. A specific non-limiting examples of a disease-specific antigen is an antigen whose expression correlates with, or is predictive of, tumor formation, for example, RCC.

Autologous: Refers to tissues, cells or nucleic acids taken from an individual's own tissues. For example, in an autologous transfer or transplantation of T cells, the donor and recipient are the same person. Autologous (or "autogeneic" or "autogenous") is related to self, or originating within an organism itself.

CD34: A cell surface glycoprotein that functions as a cell-cell adhesion molecule. CD34 is a single-pass transmembrane protein with a highly glycosylated extracellular domain, a transmembrane domain, and an intracellular signaling domain. CD34 is expressed on hematopoietic cells and plays a role in cell migration. Exemplary human CD34 sequences include GenBank Accession Nos. NM_001025109 and NM_001773 (nucleic acid sequences) and NP_001020280 and NP_001764 (amino acid sequences), all of which are incorporated herein by reference as present in GenBank on Jun. 30, 2016.

HLA-A11: An human leukocyte antigen (HLA) serotype within the HLA A group. HLA-A11 is an MHC class I molecule that includes an α chain encoded by HLA-A*11 allele group and a β chain encoded by β2-microglobulin. MHC class I molecules such as HLA-A11 bind peptides (antigens) that are typically 7-11 amino acids long and are involved in presenting the antigen to T cells via binding to a TCR.

Human endogenous retrovirus E (HERV-E): HERVs are remnants of ancient exogenous retroviruses integrated into the human genome. HERVs are estimated to comprise 5-8% of the human genome. Most HERVs have accumulated mutations or are transcriptionally silenced and do not produce full-length proteins. However, some HERVs are transcriptionally active in contexts such as tumors. HERV-E is a HERV subtype located on human chromosome 6q. At least three transcripts from HERV-E (e.g., GenBank Accession Nos. EU137846, EU137847, and JQ733905) have been identified and are expressed in RCC cells, but not in other tumors or non-tumor cells (Takahashi et al., J. Clin. Oncol. 118:1099-1109, 2008).

Operably linked: A first nucleic acid is operably linked with a second nucleic acid when the first nucleic acid is placed in a functional relationship with the second nucleic acid. For instance, a promoter is operably linked to a coding sequence if the promoter affects the transcription or expression of the coding sequence. Generally, operably linked nucleic acids are contiguous and, where necessary to join two protein coding regions, the open reading frames are aligned.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques.

Similarly, a recombinant virus is a virus with a nucleic acid sequence that is non-naturally occurring (such as including a heterologous sequence that is not from the virus) or made by artificial combination of at least two sequences of different origin. The term "recombinant" also includes nucleic acids, proteins and viruses that have been altered solely by addition, substitution, or deletion of a portion of a natural nucleic acid molecule, protein or virus.

Renal cell carcinoma (RCC): A tumor originating in the cells of the kidney. RCC is the most common type of kidney cancer in adults. There are multiple histological subtypes of RCC, including clear cell renal cell carcinoma (ccRCC), which accounts for 60-70% of RCC and originates in the cells of the proximal tubule. ccRCC cells exhibit clear cytoplasm with acinar or sarcomatoid growth pattern. Additional subtypes include but are not limited to papillary RCC (also originating in cells of the proximal tubule), chromophobic RCC (originating in cells of the cortical collecting duct), oncolytic RCC (a benign neoplasm originating in cells of the cortical collecting duct), and collecting duct RCC (originating in cells of the medullary collecting duct).

T cell: A white blood cell (lymphocyte) that is an important mediator of the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a $CD8^+$ T cell is a cytotoxic T lymphocyte (CTL). In another embodiment, a $CD8^+$ cell is a suppressor T cell.

Activated T cells can be detected by an increase in cell proliferation and/or expression of or secretion of one or more cytokines (such as IL-2, IL-4, IL-6, IFNγ, or TNFα). Activation of $CD8^+$ T cells can also be detected by an increase in cytolytic activity in response to an antigen.

In some examples, a "modified T cell" is a T cell transduced with a heterologous nucleic acid (such as one or more of the nucleic acids or vectors disclosed herein) or expressing one or more heterologous proteins. The terms "modified T cell" and "transduced T cell" are used interchangeably in some examples herein.

T cell receptor (TCR): A heterodimeric protein on the surface of a T cell that binds an antigen (such as an antigen bound to an MHC molecule, for example, on an antigen presenting cell). TCRs include α and β chains, each of which is a transmembrane glycoprotein. Each chain has variable and constant regions with homology to immunoglobulin variable and constant domains, a hinge region, a transmembrane domain, and a cytoplasmic tail. Similar to immunoglobulins, TCR gene segments rearrange during development to produce complete variable domains.

T cells are activated by binding of an antigen to a TCR and co-stimulatory signals. For example, a $CD8^+$ T cell bears T cell receptors that recognize a specific epitope when presented by a particular HLA molecule on a cell. When a CTL precursor that has been stimulated by an antigen presenting cell to become a cytotoxic T lymphocyte contacts a cell that bears such an HLA-peptide complex, the CTL forms a conjugate with the cell and destroys it.

Transduce: Transferring nucleic acid into a cell, such as transfer of a heterologous nucleic acid into a host cell. As used herein, the term transduce (or transfect or transform) include all techniques by which a nucleic acid is introduced into a cell, including but not limited to transformation with plasmid vectors, infection with viral vectors, and introduction of naked DNA by electroporation, nucleofection, lipofection, or particle gun acceleration.

A "heterologous" nucleic acid or protein refers to a nucleic acid or protein originating from a different genetic source. For example, a nucleic acid or protein that is heterologous to a cell originates from an organism or individual other than the cell in which it is expressed. In other examples, a heterologous nucleic acid or protein originates from a cell type other than the cell in which it is expressed.

Vector: A nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of an inserted gene or genes. In some non-limiting examples, the vector is a viral vector, such as a retroviral vector.

III. T Cell Receptors, Vectors, and Host Cells

Disclosed herein are T cell receptors (e.g. TCR α and β chains) cloned from a RCC HERV-E reactive T cell line. Also disclosed are vectors (such as expression vectors) including the disclosed TCRs and host cells including at least one heterologous nucleic acid encoding the disclosed TCR α and/or β chains.

A. TCRs

In some embodiments, the TCR recognizes a HERV-E peptide expressed on RCC cells, such as ATWLGSKTWK (SEQ ID NO: 1). The TCR includes α and β chain nucleic acids or polypeptides.

In some examples, the TCR α chain is encoded by a nucleic acid including or consisting of the nucleic acid sequence of SEQ ID NO: 2. In some examples, the TCR β chain is encoded by a nucleic acid including or consisting of the nucleic acid sequence of SEQ ID NO: 3. In some examples, the TCR α chain polypeptide includes or consists of the amino acid sequence of SEQ ID NO: 4. In some examples, the TCR β chain polypeptide includes or consists of the amino acid sequence of SEQ ID NO: 5.

In some embodiments, the TCR-encoding nucleic acids disclosed herein have a sequence at least 90% (for example at least 91%, 92%, 93%, 94%, 95%, 96%, 97%, 98%, or 99%, such as 100%) identical to the nucleic acid sequence of SEQ ID NO: 2 or SEQ ID NO: 3. In other embodiments, the TCR polypeptides disclosed herein have an amino acid sequence at least 95% (such as at least 96%, 97%, 98%, 99%, or 100%) identical to the amino acid sequence of SEQ ID NO: 4 or SEQ ID NO: 5. Exemplary sequences can be obtained using computer programs that are readily available on the internet and the nucleic acid and amino acid sequences set forth herein. In one example, the polypeptide retains at least one activity of the disclosed TCR polypeptides, such as binding to an RCC-specific antigenic epitope (for example, SEQ ID NO: 1), for example when expressed by a T cell in the context of both TCR α and β chains.

Minor modifications of a TCR α and/or β chain encoding nucleic acid or primary amino acid sequence may result in polypeptides which have substantially equivalent activity as compared to the unmodified counterpart polypeptide described herein. Such modifications may be deliberate, as by site-directed mutagenesis, or may be spontaneous. All of the polypeptides produced by these modifications are included herein. Thus, a specific, non-limiting example of a TCR α or β chain polypeptide is a conservative variant of the TCR α or β chain polypeptide (such as a single conservative amino acid substitution, for example, one or more conservative amino acid substitutions, for example 1-10 conservative substitutions, 2-5 conservative substitutions, 4-9 conservative substitutions, such as 1, 2, 5 or 10 conservative substitutions). A table of conservative substitutions is provided herein (Table 1). Substitutions of the amino acid sequences shown in SEQ ID NOs: 4 and 5 can be made based on this table. However, it is to be understood that non-conservative amino acid substitutions can also be made without significantly changing the activity of the polypeptide. One of ordinary skill in the art can select amino acids that can be substituted based on sequence alignments and other available sequence analysis tools.

TABLE 1

Exemplary conservative amino acid substitutions

| Original Residue | Conservative Substitution(s) |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

B. Vectors

Also disclosed herein are vectors including nucleic acids encoding HERV-E-reactive TCRs. The vectors include a nucleic acid encoding one or both of the α and β chains of the disclosed TCR (such as a nucleic acid at least 90% identical to SEQ ID NO: 2 and/or SEQ ID NO: 3) operably linked to one or more expression control elements. In particular embodiments the vector includes nucleic acids encoding both the TCR α chain (e.g., a nucleic acid encoding SEQ ID NO: 4, such as SEQ ID NO: 2) and the TCR β chain (e.g., a nucleic acid encoding SEQ ID NO: 5, such as SEQ ID NO: 3). However, in other examples, the TCR α and TCR β chains may be expressed from separate vectors. Expression control elements are sequences that control or regulate transcription and/or translation of a nucleic acid, such as promoters, enhancers, leader sequences, transcription terminators, start and/or stop codons, internal ribosome entry sites (IRES), splicing signals, and polyadenylation signals. The vector may also contain additional elements for the transfer and subsequent replication of the vector, such as origins of replication and selectable markers.

In some examples, the vector is a viral vector that includes a nucleic acid encoding at least one of the disclosed TCR α and β chains (such as a nucleic acid with at least 90% sequence identity to SEQ ID NO: 2 or SEQ ID NO: 3). In specific embodiments, the vector is a retroviral vector. Additional viral vectors suitable for gene delivery to T cells include lentivirus, adenovirus, adeno-associated virus, vaccinia virus, alphavirus, herpesvirus, and fowlpox virus vectors. In other examples, the vector is a plasmid or baculovirus vector. One of ordinary skill in the art can select an appropriate vector, for example to stably or transiently transduce T cells with the TCRs described herein.

In some embodiments, the vector is a retroviral vector including nucleic acids encoding one or both of the TCR α and β chain polypeptides disclosed herein. In particular examples, the vector is a modified retroviral vector, from which the virally encoded proteins have been deleted (for example, to prevent production of replication competent virus, reduce unwanted immunogenicity, and/or to accommodate insertion of gene(s) of interest). Exemplary retroviral backbones include those based on Moloney murine leukemia virus (MMLV), such as LXSN and SAMEN vectors (Clay et al., *Pathol. Oncol. Res.* 5:3-15, 1999). Thus, in one example, a vector is a SAMEN retrovirus vector including a nucleic acid encoding a TCR α chain having an amino acid sequence with at least 95% sequence identity to SEQ ID NO: 4 (such as a nucleic acid with at least 90% sequence identity to SEQ ID NO: 2). In another example, a vector is a SAMEN retrovirus vector including a nucleic acid encoding a TCR β chain having an amino acid sequence with at least 95% sequence identity to SEQ ID NO: 5 (such as a nucleic acid with at least 90% sequence identity to SEQ ID NO: 3). In yet another example, a vector is a SAMEN retrovirus vector including a nucleic acid encoding a TCR α chain having an amino acid sequence with at least 95% sequence identity to SEQ ID NO: 4 (such as a nucleic acid with at least 90% sequence identity to SEQ ID NO: 2) and a nucleic acid encoding a TCR β chain having an amino acid sequence with at least 95% sequence identity to SEQ ID NO: 5 (such as a nucleic acid with at least 90% sequence identity to SEQ ID NO: 3). In one non-limiting example, the vector is a SAMEN retrovirus vector including a nucleic acid encoding a TCR α chain with the amino acid sequence of SEQ ID NO: 4 (such as the nucleic acid sequence of SEQ ID NO: 2) and a nucleic acid encoding a TCR β chain with the amino acid sequence of SEQ ID NO: 5 (such as the nucleic acid sequence of SEQ ID NO: 3). In vectors where both TCR α chain and β chain nucleic acids are present, the α chain and β chain nucleic acids may be separated by an IRES or a promoter, such that both the α chain and β chain nucleic acids are transcribed and/or translated. In other examples, the α chain and β chain nucleic acids are separated by a nucleic acid encoding a peptide cleavage site or a "self-cleaving" peptide, such as a viral 2A peptide, for example, porcine teschovirus-1 2A or *Thosea asigna* virus self-cleaving peptides (see, e.g., Kim et al., *PLoS One* 6:e18556, 2011).

In additional embodiments, the vector further includes a nucleic acid encoding a selectable marker that allows identification and/or enrichment of cells transduced with the vector. Exemplary selectable markers include antibiotic resistance genes (such as neomycin resistance), thymidine kinase, fluorescent proteins (such as green fluorescent protein), or β-galactosidase. In other examples, a selectable marker includes a cell surface expressed protein that can be used to identify transduced cells (for example, using flow cytometry or immuno-magnetic separation). In one non-limiting example, the vectors disclosed herein include a nucleic acid encoding a truncated CD34 protein (CD34t) lacking the intracellular signaling domain. The CD34t protein includes the extracellular and transmembrane regions of CD34, and as a result, it is expressed on the cell surface, but does not affect activity of cells expressing the truncated protein (Norell et al., *Cancer Immunol. Immunother.* 59:851-862, 2010). Cells expressing CD34t can be identified with an anti-CD34 antibody, and can be isolated using flow cytometry or immuno-magnetic methods.

In one example, a nucleic acid encoding CD34t includes or consists of the sequence of nucleotides 4028-4975 of SEQ ID NO: 6 or a sequence having at least 95% (such as at least 95%, 96%, 97%, 98%, 99%, or more) sequence identity with nucleotides 4028-4975 of SEQ ID NO: 6. In particular examples, the CD34t protein includes or consists of an amino acid sequence having at least 95% (such as at least 95%, 96%, 97%, 98%, 99%, or 100%) sequence identity with the amino acid sequence of SEQ ID NO: 7.

An exemplary retroviral vector (such as a SAMEN vector) for expressing the disclosed TCR α and β chains is shown in FIG. 1. The vector includes a 5' long terminal repeat (LTR) including a promoter/enhancer (such as a human cytomegalovirus promoter/enhancer fused to a MMLV 5' LTR), a packaging signal (ψ), a nucleic acid encoding the TCR α chain (e.g., SEQ ID NO: 2), a first self-cleaving 2A peptide (such as a porcine teschovirus self-cleaving 2A (P2A) peptide), a nucleic acid encoding the TCR β chain (e.g., SEQ ID NO: 3), a second self-cleaving 2A peptide (such as a *Thosea asigna* self-cleaving 2A (T2A) peptide), a nucleic acid encoding a truncated CD34 protein, and a 3' LTR.

In some examples, the vector includes or consists of the nucleic acid sequence of SEQ ID NO: 6. In other examples, the vector includes or consists of a nucleic acid sequence having at least 95% (such as at least 95%, 96%, 97%, 98%, 99%, or 100%) sequence identity with the nucleic acid sequence of SEQ ID NO: 6. In the exemplary vector provided herein, the TCRα chain is encoded by nucleotides 2165-2971 of SEQ ID NO: 6, the P2A peptide is encoded by nucleotides 2972-3037 of SEQ ID NO: 6, the TCRβ chain is encoded by nucleotides 3038-3958 of SEQ ID NO: 6, the T2A peptide is encoded by nucleotides 3959-4027 of SEQ ID NO: 6, and the CD34t receptor is encoded by nucleotides 4028-4975 of SEQ ID NO: 6.

C. Host Cells

Also disclosed herein are host cells that include a nucleic acid encoding a disclosed TCR α chain and/or a disclosed TCR β chain, such as a vector encoding the TCR α chain, the TCR β chain, or both. In some examples, the host cell is a cell capable of producing recombinant virus including the vector (e.g., a producer cell). In other examples, the host cell is a lymphocyte (for example, a T cell). Methods of introducing a vector into a host cell are known to one of ordinary skill in the art and include transformation (e.g. with plasmid vectors), infection (e.g., with viral vectors), and electroporation, nucleofection, lipofection, or particle gun acceleration (e.g., naked DNA).

In examples where the TCR α and/or β chains are expressed from a retroviral vector (such as the disclosed SAMEN vectors), production of recombinant virus requires viral proteins expressed from a helper virus or a packaging cell line. Therefore, in some examples, a viral vector disclosed herein is introduced into a host cell (such as a 293 cell line) with a helper virus expressing viral proteins (such as gag, pol, and/or env). In other examples, a viral vector disclosed herein is transduced into a packaging cell line that stably expresses viral gag, pol, and env proteins. Exemplary packaging cell lines include NIH-3T3 cell lines, such as GP&E 86, PG13, and PA317 cell lines (Markowitz et al., *J. Virol.* 62:1120-1124, 1988; Miller et al., *J. Virol.* 65:2220-2224, 1991; Miller et al., *Mol. Cell Biol.* 6:2895-2902, 1986) or 293 cell lines, such as 293GPG cells, GP2-293 cells. Thus, in one embodiment, a host cell is a producer cell, such as packaging cell line transduced with a viral vector described herein. In one non-limiting example, the viral vector is a SAMEN vector encoding a HERV-E specific TCR α chain and β chain and a truncated CD34 protein (such as a vector with the nucleic acid of SEQ ID NO: 6). In some examples, the producer cell line is GMP qualified. In one example, a producer cell line is a PG13 packaging cell line including a SAMEN vector encoding a HERV-E specific TCR α chain and β chain and a truncated CD34 protein (such as a vector with the nucleic acid of SEQ ID NO: 6).

In some examples, the host cell is a lymphocyte, such as a T cell. In some embodiments, the lymphocytes are T cells (such as a population of enriched or expanded T cells) that include a heterologous nucleic acid encoding at least one of the disclosed TCR α and β chains. In some examples, the lymphocytes include a heterologous nucleic acid encoding a TCR α chain having an amino acid sequence with at least 95% sequence identity to SEQ ID NO: 4 (such as a nucleic acid with at least 90% sequence identity to SEQ ID NO: 2). In another example, the lymphocytes include a heterologous nucleic acid encoding a TCR β chain having an amino acid sequence with at least 95% sequence identity to SEQ ID NO: 5 (such as a nucleic acid with at least 90% sequence identity to SEQ ID NO: 3). In yet another example, the lymphocytes include a heterologous nucleic acid encoding a TCR α chain having an amino acid sequence with at least 95% sequence identity to SEQ ID NO: 4 (such as a nucleic acid with at least 90% sequence identity to SEQ ID NO: 2) and a nucleic acid encoding a TCR β chain having an amino acid sequence with at least 95% sequence identity to SEQ ID NO: 5 (such as a nucleic acid with at least 90% sequence identity to SEQ ID NO: 3). In one non-limiting example, the lymphocytes include a heterologous nucleic acid encoding a TCR α chain with the amino acid sequence of SEQ ID NO: 4 (such as the nucleic acid sequence of SEQ ID NO: 2) and a nucleic acid encoding a TCR β chain with the amino acid sequence of SEQ ID NO: 5 (such as the nucleic acid sequence of SEQ ID NO: 3). In additional examples, the lymphocytes also include a heterologous nucleic acid encoding a truncated CD34 protein (for example, a CD34 protein lacking the intracellular or signaling domain).

In some embodiments, the lymphocytes (such as a population of lymphocytes) are transduced with a vector disclosed herein. Following transduction, expression of the TCR α chain and/or β chain can be determined by methods known to one of ordinary skill in the art, such as flow cytometry using a labeled antibody or detecting reactivity to the cognate peptide (such as SEQ ID NO: 1). In some examples, if the TCR α and/or β chain is co-expressed with CD34t, transduced cells can also be detected and/or enriched using an anti-CD34 antibody, for example, utilizing flow cytometry or immuno-magnetic techniques (e.g., CliniMACS® CD34 reagent system, Miltenyi Biotec Inc., San Diego, Calif. or Isolex® 300 magnetic cell selection system, Nexell Therapeutics Inc., Irvine, Calif.).

In some embodiments, modified (e.g., transduced) T cells expressing the disclosed TCR α and β chains are produced by obtaining a population of lymphocytes (such as a population of PBMCs) from a subject, for example by apheresis. Naïve or quiescent T cells in the population of lymphocytes are activated prior to transduction, for example, by contacting the lymphocytes with one or more cytokines (such as one or more of IL-2, IL-4, IL-6, IL-7, IL-12, IL-15, and IL-23). In some examples, the lymphocytes are contacted with anti-CD3 antibody and IL-2 for 1-4 days (such as 1 day, about 2 days, about 3 days, or about 4 days) to produce activated T cells. In some examples, the lymphocytes are contacted with 30 ng/ml anti-CD3 antibody and 300 IU/ml IL-2 for 2 or 3 days.

The activated T cells are transduced with a vector disclosed herein, for example, by infection (in the case of a viral vector) or by transfection or transformation (in the case of a plasmid or naked DNA vector). In some examples, the transduced T cells are enriched and/or expanded. For example, if the vector includes a nucleic acid encoding a truncated CD34 molecule, transduced T cells can be selected or enriched by contacting the population of transduced T cells with an anti-CD34 antibody and purifying CD34-expressing cells (for example, using flow cytometry or immuno-magnetic beads), for example about 2-4 days after transduction. The transduced T cells can also be expanded by culturing the transduced T cells with anti-CD3 (e.g., about 30 ng/ml), anti-CD28 (e.g., about 30 ng/ml), and/or IL-2 (e.g., about 300 IU/ml) for a period of time (such as about 7-14 days or 9-11 days). In some examples, the transduced T cells are expanded by culture on irradiated PBMC cells.

IV. Methods of Treating or Inhibiting Renal Cell Carcinoma

Disclosed herein are methods of treating or inhibiting RCC in a subject by administering to the subject a T cell (or population of T cells) expressing a TCR (for example, TCR α and β chains) that bind to an antigen or epitope expressed by RCC cells. In some examples, the methods include administering the modified T cells described herein to a subject with RCC (such as ccRCC, advanced ccRCC, or metastatic ccRCC). In particular examples, the subject is HLA-A11 positive and has ccRCC.

The modified lymphocytes (e.g., modified or transduced T cells) described herein can be incorporated into pharmaceutical compositions. In some examples, the composition includes about $10^4$ to $10^{12}$ of the modified T cells (for example, about $10^4$-$10^7$ cells, about $10^6$-$10^9$ cells, or about $10^8$-$10^{12}$ cells). For example, the composition may be prepared such that about $5 \times 10^6$ to $5 \times 10^8$ modified T cells/kg are administered to a subject. Such compositions typically include a population of modified T cells and a pharmaceutically acceptable carrier. A "pharmaceutically acceptable carrier" includes any and all solvents, dispersion media, coatings, antibacterial and antifungal agents, isotonic and absorption delaying agents, and the like, compatible with pharmaceutical administration. Examples of such carriers or diluents include, but are not limited to, water, saline, Ringer's solutions, dextrose solution, and 5% human serum albumin Liposomes and non-aqueous vehicles such as fixed oils may also be used. Supplementary active compounds can also be incorporated into the compositions. Actual methods for preparing administrable compositions are known or apparent to those skilled in the art and are described in more detail in such publications as *Remington: The Science and Practice of Pharmacy*, The University of the Sciences in Philadelphia, Editor, Lippincott, Williams, & Wilkins, Philadelphia, Pa., 21$^{st}$ Edition (2005).

In vivo treatment of a subject is initiated by administration of the modified T cells disclosed herein. Administration is typically via intravenous or intraperitoneal infusion, although direct injection into solid tumors or other such focal lesions can also be used. The efficacy of the treatment is generally assessed by lesion reduction/clearance (for example, using RECIST criteria). Lesion size and number can be evaluated by imaging (such as MRI, PET, and/or CT imaging). In some examples, staging is done every month, every 3 months, or every 6 months. In some examples, blood samples from the subject are also analyzed at one or more time points following infusion to quantitate the number of modified T cells present (for example, by assessing absolute number and/or percentage of CD3+ cells expressing CD34, in the case of CD34t-expressing modified T cells).

Multiple doses of the population of modified T cells can be administered. For example, the population of modified T cells can be administered daily, every other day, twice per week, weekly, every other week, every three weeks, monthly, or less frequently. In one specific example, a single infusion of modified T cells is administered; however, a skilled clinician can select alternative schedules based on the subject, the condition being treated, the previous treatment history, and other factors.

In some embodiments, the subject has RCC, such as ccRCC. Methods of identifying a subject with RCC or ccRCC are known to one of ordinary skill in the art and include radiographic evidence of RCC (for example, imaging by ultrasound, MRI, CT scan, or PET scan) and/or a biopsy (such as a fine needle aspirate or needle core biopsy) confirming presence of RCC. In some examples, the subject has metastatic RCC. In additional examples, the subject with RCC also is HLA A11+ and the tumor expresses a HERV-E provirus (for example, expresses a protein comprising the amino acid sequence of SEQ ID NO: 1). In some embodiments, the methods include selecting a patient with RCC (such as ccRCC) who is HLA A11+ and whose tumor expresses a protein comprising SEQ ID NO: 1 for treatment with the modified T cells.

In particular embodiments, the methods include obtaining a population of cells including lymphocytes from a subject with RCC (such as a subject with ccRCC who is HLA A11+ and whose tumor expresses HERV-E provirus, such as a protein comprising SEQ ID NO: 1). In other examples, a population of cells including lymphocytes are obtained from an HLA-matched donor to the subject to be treated (such as a subject with ccRCC who is HLA A11+ and whose tumor expresses HERV-E provirus, such as a protein comprising SEQ ID NO: 1).

An exemplary protocol for collecting and transducing T cells from a subject is shown in FIG. A population of cells including lymphocytes (such as PBMCs) can be obtained by any method, including, but not limited to apheresis. All or a portion of the population of cells can be utilized immediately or all or a portion of the cells can be cryopreserved for future use. When ready for use, all or a portion of the population of cells is thawed (if previously cryopreserved) and T cells are activated by incubation with an anti-CD3 antibody (such as OKT3). In some examples, about $10^7$-$10^9$ PBMCs are incubated with an anti-CD3 monoclonal antibody (e.g., about 30 ng/ml) and optionally also IL-2 (e.g., about 300 IU/ml) and/or IL-15 (about 10-100 ng/ml). In one specific example, about $6\times10^8$ PBMCs are incubated with anti-CD3 antibody OKT3 and IL-2 for about 1-5 days (such as about 1 day, about 2 days, about 3 days, about 4 days, or about 5 days). In another specific example, about $6\times10^8$ PBMCs are incubated with anti-CD3 antibody OKT3, IL-2, and IL-15 for about 1-5 days (such as about 1 day, about 2 days, about 3 days, about 4 days, or about 5 days).

In some examples, following T cell activation, the cells are optionally depleted of CD4+ cells. In some examples, CD4+ cells are removed using an anti-CD4 antibody, for example, utilizing flow cytometry or immuno-magnetic techniques (e.g., CliniMACS® CD4 reagent system, Miltenyi Biotec Inc., San Diego, Calif.) or erythrocyte resetting of CD4+ T-cells bound by anti-CD4 antibodies, to produce a CD4-depleted cell population. In other examples, CD4 depletion can be carried out after transduction or after expansion of the transduced T cells. In some examples, the CD4-depleted cell population is a CD8+ population of T cells (for example, a population of T cells that is substantially CD8+ T cells, such as a population of T cells that is at least 80%, 85%, 90%, 95%, 96%, 97%, 98%, 99%, or more CD8+ T cells).

Following T cell activation (and optional CD4+ cell depletion) the cells are transduced with a vector including a heterologous nucleic acid encoding the HERV-E reactive TCR α chain, T cell β chain, or both (such as one or more of the vectors described in Section IIIB, above). In particular examples, about $10^7$-$10^9$ cells are transduced (for example, about $1\times10^7$, $5\times10^7$, $1\times10^8$, $5\times10^8$, or $1\times10^9$ cells). In one non-limiting example, about $2\times10^8$ cells are transduced. In some examples, the vector also includes a heterologous nucleic acid encoding a truncated CD34 protein. Thus, in some examples, transduced T cells are enriched using a CD34-specific antibody (such as flow cytometry or immuno-magnetic purification).

Transduced T cells (or optionally, CD34-enriched transduced T cells and/or CD34-enriched, CD4-depleted transduced T cells) are expanded ex vivo and can be cryopreserved at appropriate dosage amounts (for example, about $10^6$ to $10^{12}$ cells) following expansion. In one specific example, the transduced T cells are expanded on irradiated allogeneic PBMC feeder cells (40 million cells per 250,000 T cells) in medium containing 300 IU/ml IL-2, 30 ng/ml anti-CD3, and 30 ng/ml anti-CD28. The expansion can be for a sufficient time to obtain the desired number of T cells, for example, about 4-14 days (such as 4-9 days, 7-10 days, 8-12 days, 9-14 days, 9-11 days). In some examples, the T cells are supplemented with fresh IL-2 on days 5, 8, and 11. In some non-limiting examples, the expansion can optionally be carried out in a WAVE bioreactor (GE Healthcare Life Sciences, Pittsburgh, Pa.) for at least a portion of the expansion, such as for 1-5 days, for example from days 9-14 of the expansion protocol. One of ordinary skill in the art can identify other methods for expanding T cells ex vivo, which can also be used with the transduced T cells described herein (see, e.g., U.S. Pat. No. 5,827,642 and Riddell and Greenberg, *J. Immunol. Meth.* 128:189-201, 1990, incorporated herein by reference in their entirety).

The transduced (modified) T cells are thawed (if previously frozen), prior to administration to the subject. The subject may undergo an immunosuppressive regimen (e.g., lymphodepletion) prior to administering the modified T cells. In one example, the subject is administered cyclophosphamide and/or fludarabine prior to administering the modified T cells. In one non-limiting example, the subject is administered cyclophosphamide (e.g., 60 mg/kg) on days −5 and −4 and/or fludarabine (e.g., 25 mg/m$^2$) on days −5 through −1 (where day 0 is administration of the modified T cells). In another non-limiting example, the subject is administered cyclophosphamide (1,000 mg/m$^2$ IV) on day −5 and fludarabine (30 mg/m$^2$) on days −5 through −3 (where day 0 is administration of the modified T cells). The modified T cells are administered to the subject, for example by infusion. In some examples, the T cells are administered at a dose of about $10^4$ to $10^{12}$ of the modified T cells (for example, about $10^4$-$10^7$ cells, about $10^6$-$10^9$ cells, or about $10^8$-$10^{12}$ cells or about $1\times10^6$ to $1\times10^9$ modified T cells/kg (such as about $1\times10^6$, $5\times10^6$, $1\times10^7$, $5\times10^7$, $1\times10^8$, $5\times10^8$, or $1\times10^9$ cells/kg) Immune system supportive therapies may also be administered to the subject, for example to promote expansion of the modified T cells in the subject and/or to support recovery of neutrophils. In one non-limiting example, the subject is administered IL-2 (e.g., 72,000 iu/kg iv every 8 hours) for 10 days and/or G-CSF (e.g., 300-480 μg sc) daily from day+1 until absolute neutrophil count is greater than 500. In another example, the immune system supportive therapy includes administering $2\times10^6$ i.u./m² every 12 hours for seven days following administration of the modified T cells.

Treatment efficacy is monitored by standard methods such as tumor size, number of lesions, tumor stage, response rate, or other criteria known to one of ordinary skill in the art. In some examples, a decrease in size of primary tumor or metastases (for example, as defined by standard RECIST or irRECIST criteria) indicates inhibition of RCC in the subject. See, e.g., Eisenhauer et al., *Eur. J. Cancer* 45:228-247, 2009; Wolchock et al., *Clin. Cancer Res.* 15:7412-7420, 2009; both of which are incorporated herein by reference. In other examples, progression-free survival and/or overall survival (for example, for 1 month, 3 months, 6 months, 9 months, 12 months, 18 months 2 years, or more, such as 1-12 months, 6-18 months, 1-2 years, or more) indicates inhibition of RCC in the subject. In other examples, one or more of persistence of circulating HERV-E TCR transduced CD34+ or CD8+/CD34+ T cells, changes in immune cell subsets and activation status of T cells, as well as other immunologic determinants are evaluated, with clinical outcomes at baseline, at different time points during treatment, and at the time of disease progression.

In some examples, the subject is also administered one or more additional treatments, such as one or more therapeutic agents, surgical resection, and/or radiation therapy before, concurrently, or after treatment with the transduced T cells. One of skill in the art can select therapeutic agents for administration to a subject with RCC in combination with the modified T cells disclosed herein. Such agents include anti-VEGF agents (such as pazopanib, sorafenib, sunitinib, axitinib, cabozantinib, sorafenib, lenvatinib. and/or bevacizumab), mTOR inhibitors (such as temsirolimus and/or everolimus), immune checkpoint inhibitors (such as nivolumab), and/or cytokine therapy (such as IFNα and/or IL-2).

EXAMPLES

The following examples are provided to illustrate certain particular features and/or embodiments. These examples should not be construed to limit the disclosure to the particular features or embodiments described.

Example 1

Cloning of T Cell Receptor from HERV-E CT-RCC1 Reactive CD8+ T Cells

A CD8+ HLA-A11 restricted RCC-reactive T cell clone was previously identified (Takahashi et al., *J. Clin. Invest.* 118:1099-1109, 2008). This RCC reactive CTL recognizes the HERV-E peptide ATWLGSKTWK (SEQ ID NO: 1) (Takahashi et al., 2008). Total RNA was extracted from the T cell clone with HLA-A11 restricted recognition of ccRCC cells and full length TCR chains were identified by 5' RACE. The nucleic acids encoding the TCR α and β chains are disclosed herein as SEQ ID NOs: 2 and 3, respectively. The amino acid sequence of the TCR α and β chains are disclosed herein as SEQ ID NOs: 4 and 5, respectively.

The TCR α and β chain-encoding nucleic acids (SEQ ID NOs: 2 and 3) were cloned into a retroviral construct including a truncated CD34 molecule linked to the β chain (FIG. 1). The truncated CD34 cassette includes the extracellular and transmembrane domains but lacks the intracellular signaling domain so it does not function in cells, but its expression allows enrichment of transduced T cells based on their surface expression of CD34. The sequence of the vector is provided as SEQ ID NO: 6.

Example 2

Figure 3A:
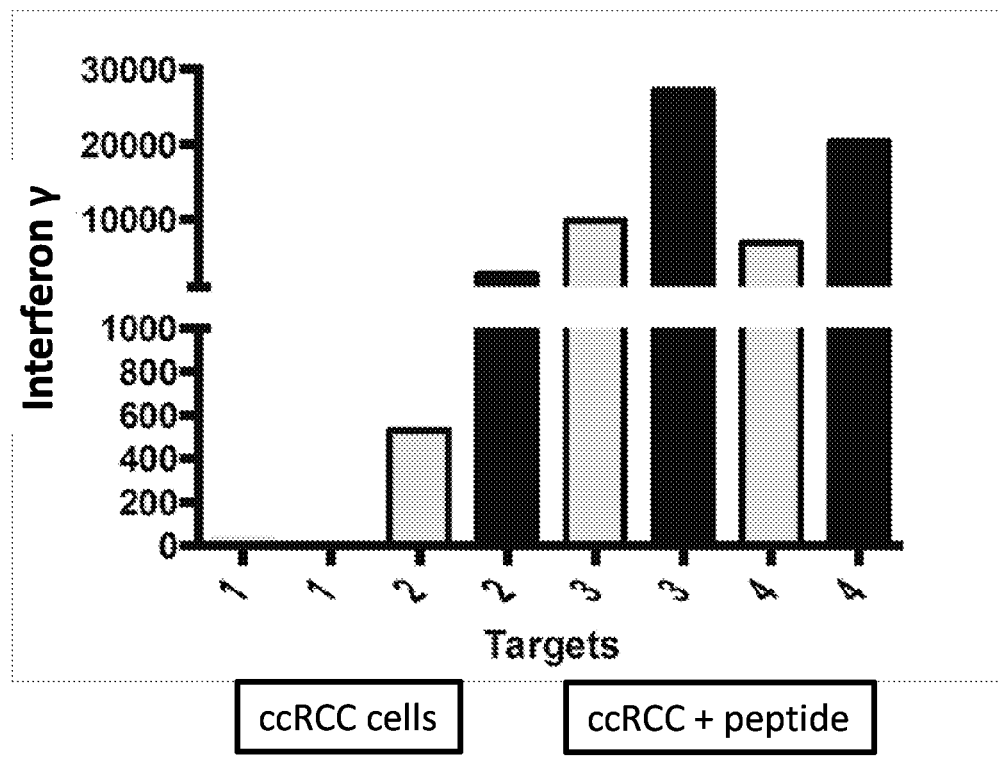
FIGS. 3A and 3B are graphs showing reactivity of T cells transduced with a retroviral vector encoding the HLA-A11 restricted TCR against ccRCC cells from two donors (FIG. 3A) and from one donor (FIG. 3B).
Figure 3B:
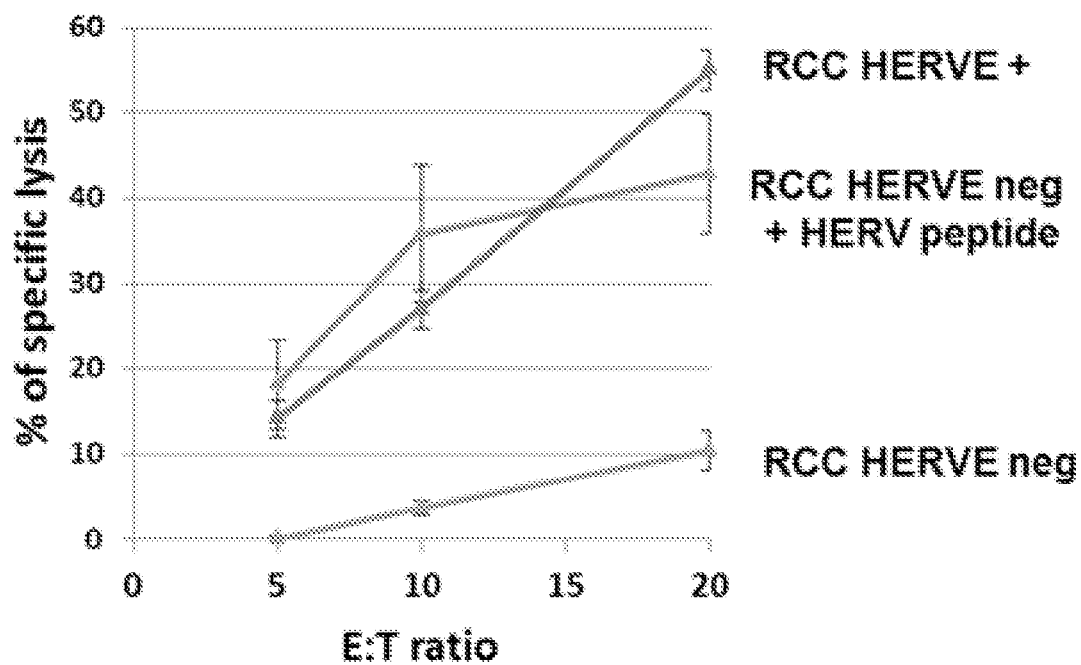

Reactivity of T Cells Transduced with HLA-A11 Restricted TCR Against ccRCC Cells PBMCs from two healthy donors were transduced with the vector described in Example 1. The transduced T cells specifically killed HLA-A11+ and HERV-E+ ccRCC cells (FIGS. 3A and 3B). Addition of the CT-RCC-1 peptide (SEQ ID NO: 1) increased reactivity against both HERV-E negative and HERV-E positive cells, as expected (FIGS. 3A and 3B).

Example 3

Development of Producer Clones

The retroviral vector containing this TCR described in Example 1 was introduced into the PG13 packaging cell line to isolate high titer retroviral producer clones for clinical use. The PG13 producer cell line was cloned in limiting dilution to generate high titer clones. Then, the clones were screened for their ability to efficiently transduce and transfer anti-HERV-E reactivity to human T cells. Two clones were selected (7G1 and 27A7) for further testing.

For this purpose, retrovirus was prepared from each clone and two separate full scale validation runs were performed. T cells from 2 healthy donors were transduced with retrovirus from clone 7G1 or 27A7. They were 63.2% and 67.5% ($\overline{X}$=65.4%) or 65.2% and 61.6% ($\overline{X}$=63.4%) CD34+, respectively, indicating both clones transduced T cells with equal efficiency. Following CD34 purification of the transduced cells using immune-magnetic beads, the cultures were 99.3% and 98.4% ($\overline{X}$=98.9%) or 99.4% and 99.7% ($\overline{X}$=99.6%) CD34+ respectively indicating pure TCR transduced T cell cultures.

Master Cell banks of $5\times10^6$ cells per vial were generated for both clones (212 vials for 7G1 and 220 vials 27A7). A large 3-liter batch of virus was prepared from the 7G1 clone and both the 7G1 clone and 7G1 virus were sent to the Vector Production Facility/National Gene Vector Biorepository at Indiana University for GMP qualification.

Example 4

Evaluation of HERV-E TCR Transduced T Cells

Figure 4A:
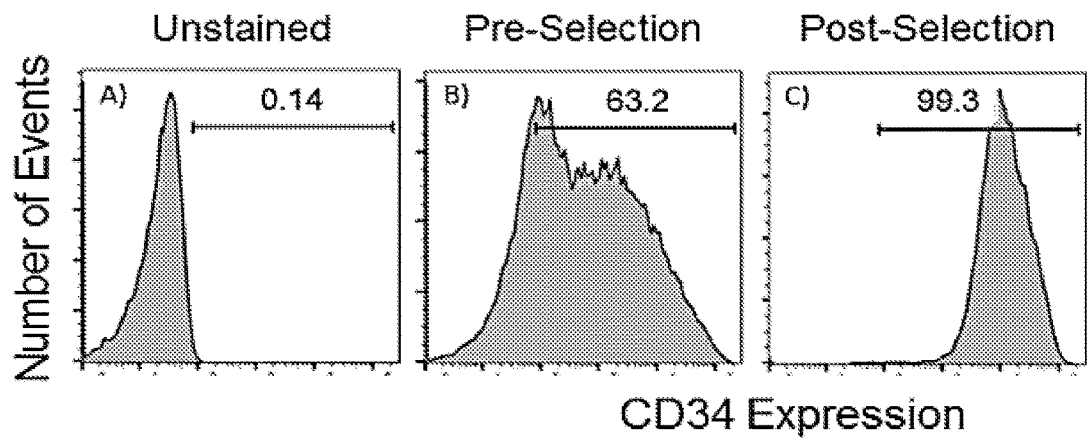
FIGS. 4A-4C are a series of plots showing CD34 expression in transduced T cells pre- and post-CD34 selection step (FIG. 4A) and CD3 (FIG. 4B) and HERV-E tetramer (FIG. 4C) expression in CD34-selected transduced T cells.
Figure 4B:
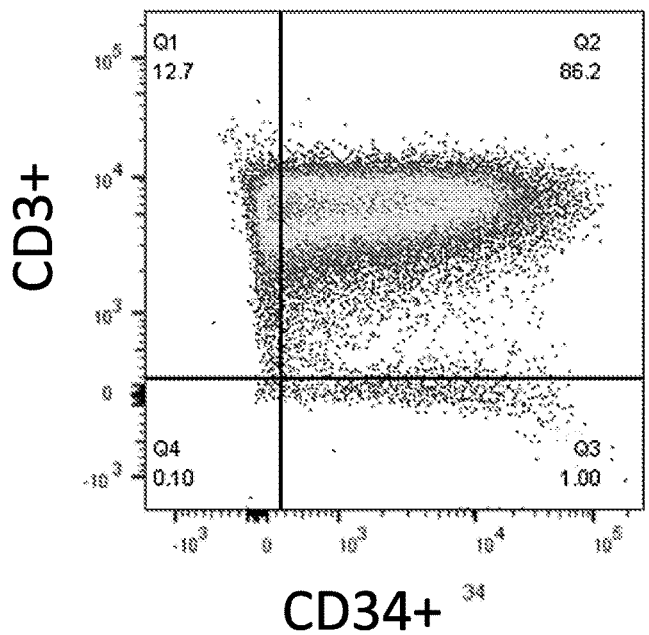
Figure 4C:
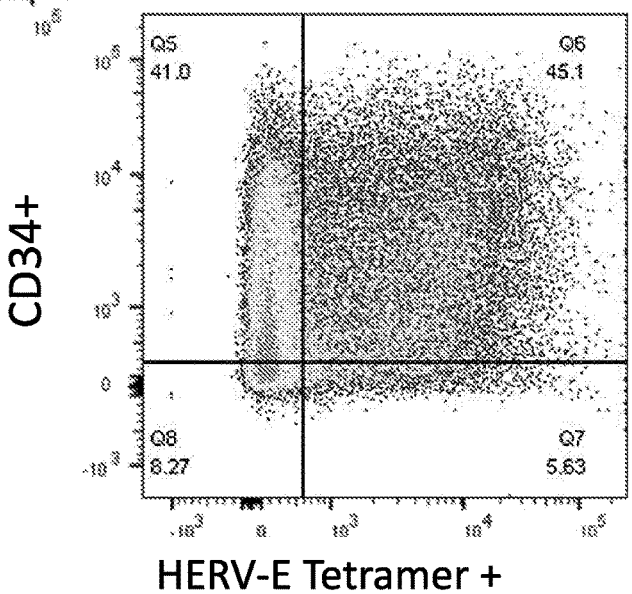
Figure 5A:
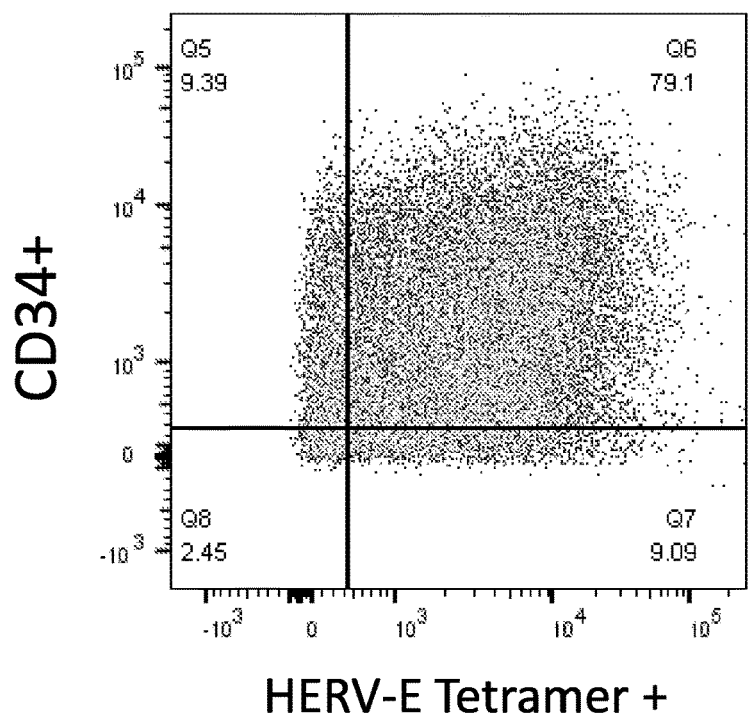
FIGS. 5A and 5B are plots showing CD8 (FIG. 5A) and CD4 (FIG. 5B) cells in CD34$^+$-HERV-E tetramer$^+$ transduced T cells.
Figure 5B:
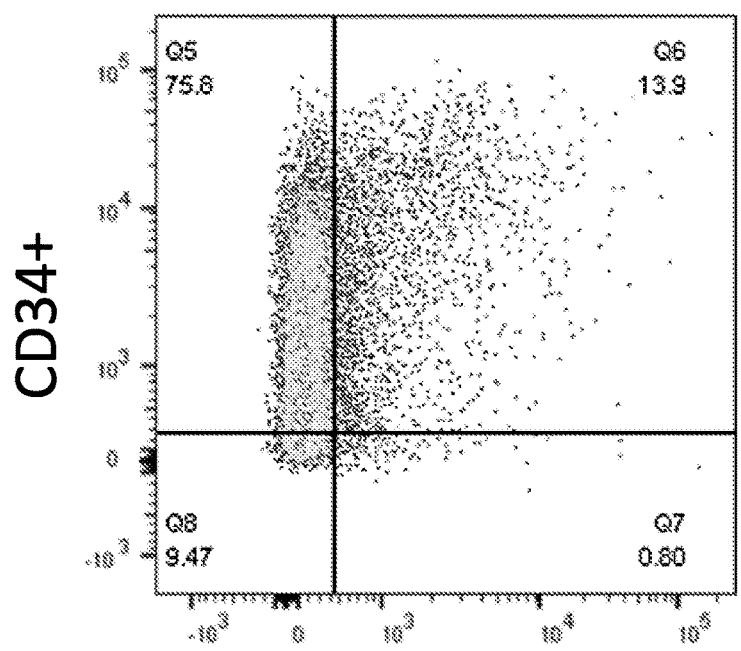

Supernatants from the PG13 retroviral producer clone 7G1 were used to transduce normal PBL-derived T cells. Three days post-transduction, the cells were incubated with anti-CD34 coated immunomagnetic particles and purified using the CliniMACS and stained for CD34 expression. Prior to selection 63.2% of the cells expressed CD34; this was increased to 99.3% post-selection (FIG. 4A). The CD34+ cells expressed CD3 (FIG. 4B) and stained positively with the HERV-E tetramer (FIG. 4C). The CD34-selected cells were primarily CD8+ cells (FIG. 5A), with only a small fraction of CD4+ cells (FIG. 5B).

Figure 6A:
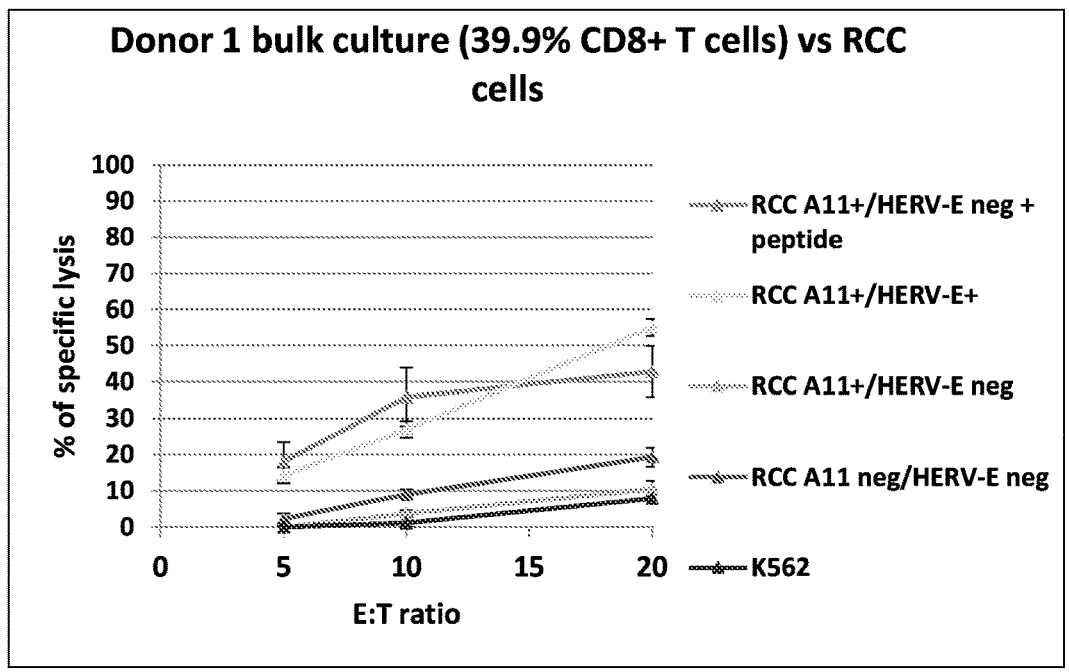
FIGS. 6A and 6B are graphs showing chromium cytotoxicity of T cells transduced with a retroviral vector encoding the HLA-A11 restricted TCR against ccRCC cells from two donors. The T cell population from donor 1 was 39.9% CD8$^+$ (FIG. 6A) and the T cell population from donor 2 was 52.8% CD8$^+$ (FIG. 6B).
Figure 6B:
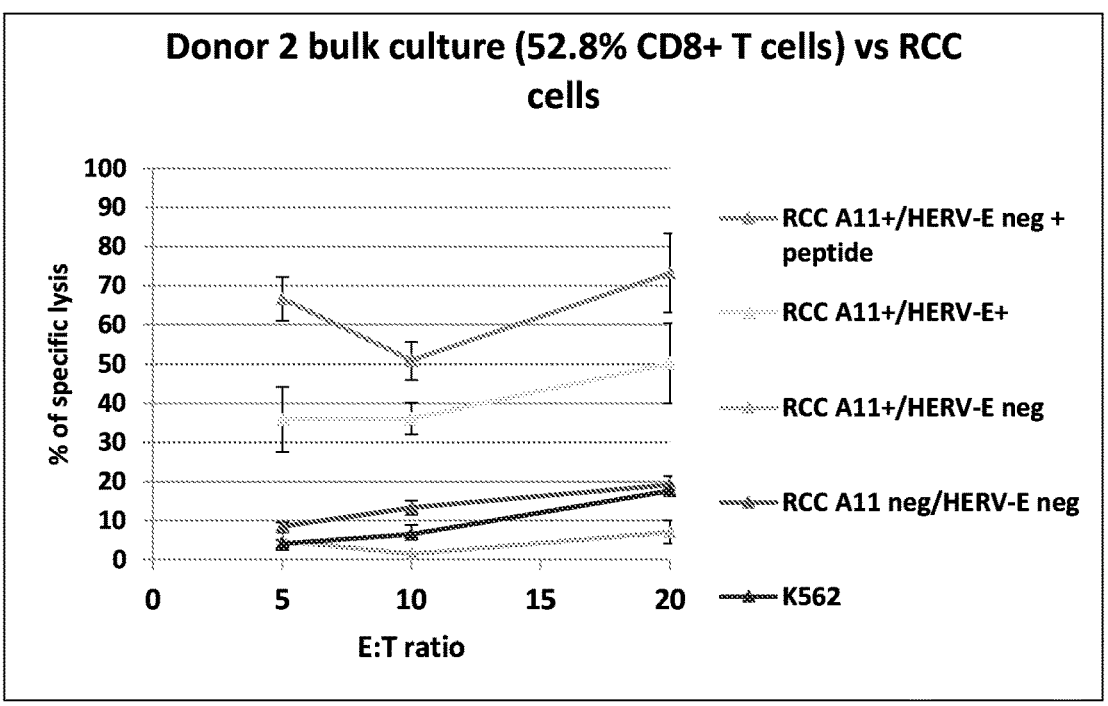

Transduced T cells as described in Example 2 were evaluated. As determined by chromium release cytotoxicity, the transduced T cells specifically killed HLA-A11+ and HERV-E+ ccRCC cells (FIGS. 6A and 6B). Addition of the CT-RCC-1 peptide (SEQ ID NO: 1) increased reactivity against HERV-E negative cells (FIGS. 6A and 6B). The T cell population from donor 1 was 39.9% CD8+ (FIG. 6A) and the T cell population from donor 2 was 52.8% CD8+ (FIG. 6B).

Figure 7:
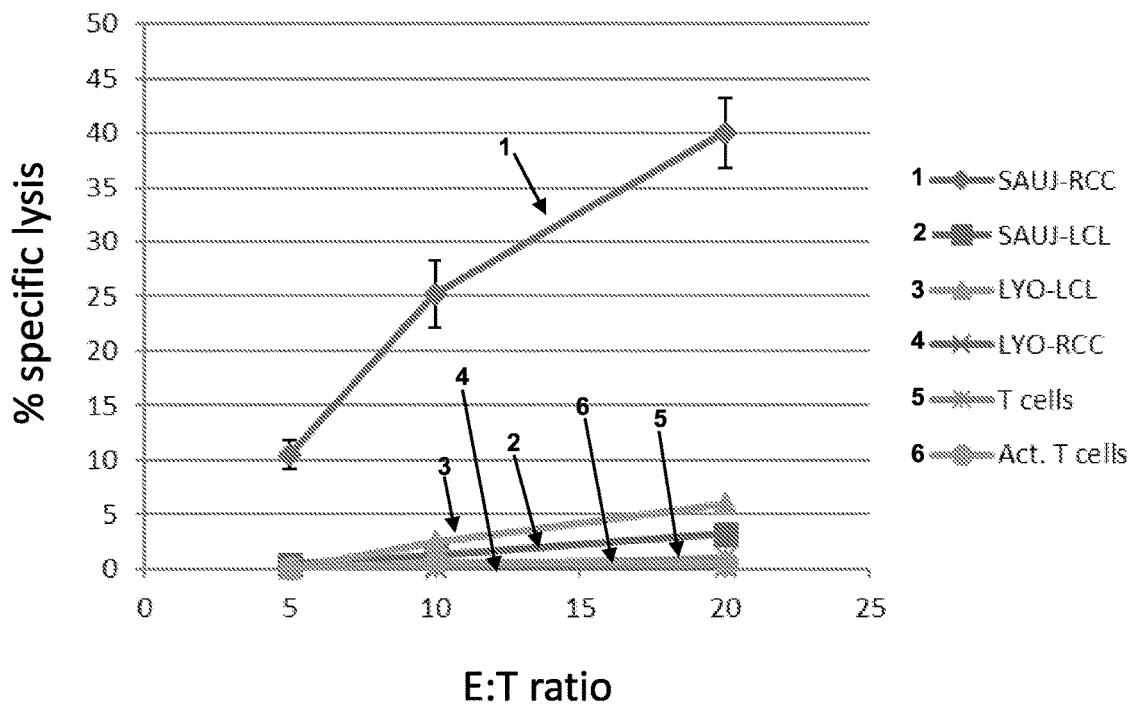
FIG. 7 is a graph showing chromium release cytotoxicity of T cells transduced with a retroviral vector encoding the HLA-A11 restricted TCR against RCC or LCL cells from two different donors and against T cells and activated T cells from a HLA-A11 negative donor.

PBMC from a healthy donor transduced with the vector described in Example 1 were also tested for specific killing of RCC cells and T cells. HLA-A11+ and HERV-E expressing SAUJ-RCC cells were specifically killed, while HLA-A11−HERV-E negative cells (SAUJ-LCL) were not (FIG. 7). HLA-A11− cells also were not killed whether they expressed HERV-E (LYO-RCC) or not (LYO-LCL). Finally, T cells from an HLA-A11+ donor were not killed (FIG. 7).

Figure 8:
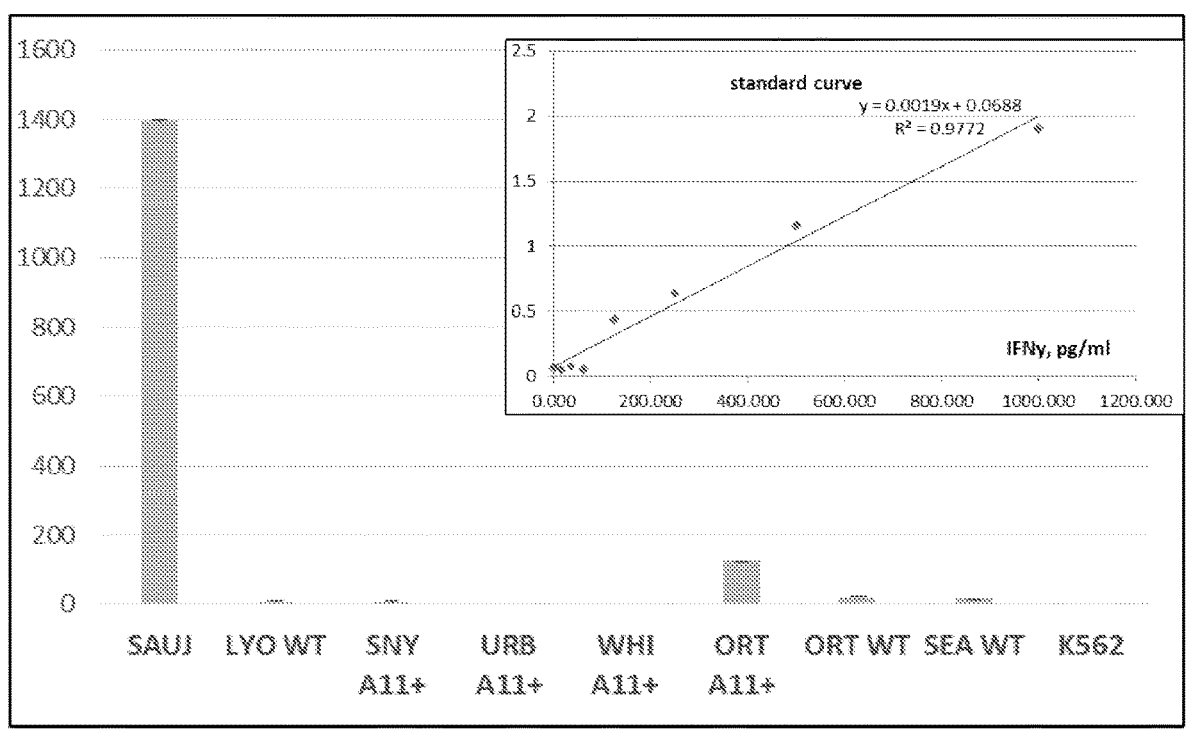
FIG. 8 is a graph showing interferon-γ (IFNγ) secretion using CD8+CD34+ T cells from a healthy donor transduced with a retroviral vector encoding the HLA-A11 restricted TCR contacted with various cell lines. The HERV-E/HLA-A11 status of each cell line is as follows: SAUJ: HERV-E+/HLA-A11+; LYO WT: HERV-E+/HLA-A11neg; SNY A11+: HERV-E neg/HLA-A11-transduced; URB A11+; HERV-E neg/HLA-A11-transduced; WHI A11+: HERV-E neg/HLA-A11-transduced; ORT A11+: HERV-E neg/HLA-A11-transduced; ORT WT: HERV-E neg/HLA-A11neg; SEA WT: HERV-E neg/HLA-A11neg. A standard curve is shown in the inset.

Antigen specificity of HERV-E TCR transduced T cells was evaluated by measuring interferon-γ (INF-γ) secretion by enzyme-linked immunosorbent assay (ELISA) using a panel of ccRCC cell lines as targets. FIG. 8 shows that transduced T cells produce INF-γ only when co-culturing with both HLA-A11-positive and CT-RCC HERV-E-expressing ccRCC cells (>twice background and >1 ng/ml).

Example 5

Determining Safety and Tolerability of HERV-E TCR Transduced T Cells

This example describes methods that can be used to determine safety and tolerability of treating ccRCC with HERV-E TCR transduced T cells. However, one skilled in the art will appreciate that methods that deviate from these specific methods can also be used to successfully determine safety and tolerability of the HERV-E TCR transduced T cells.

Figure 9:
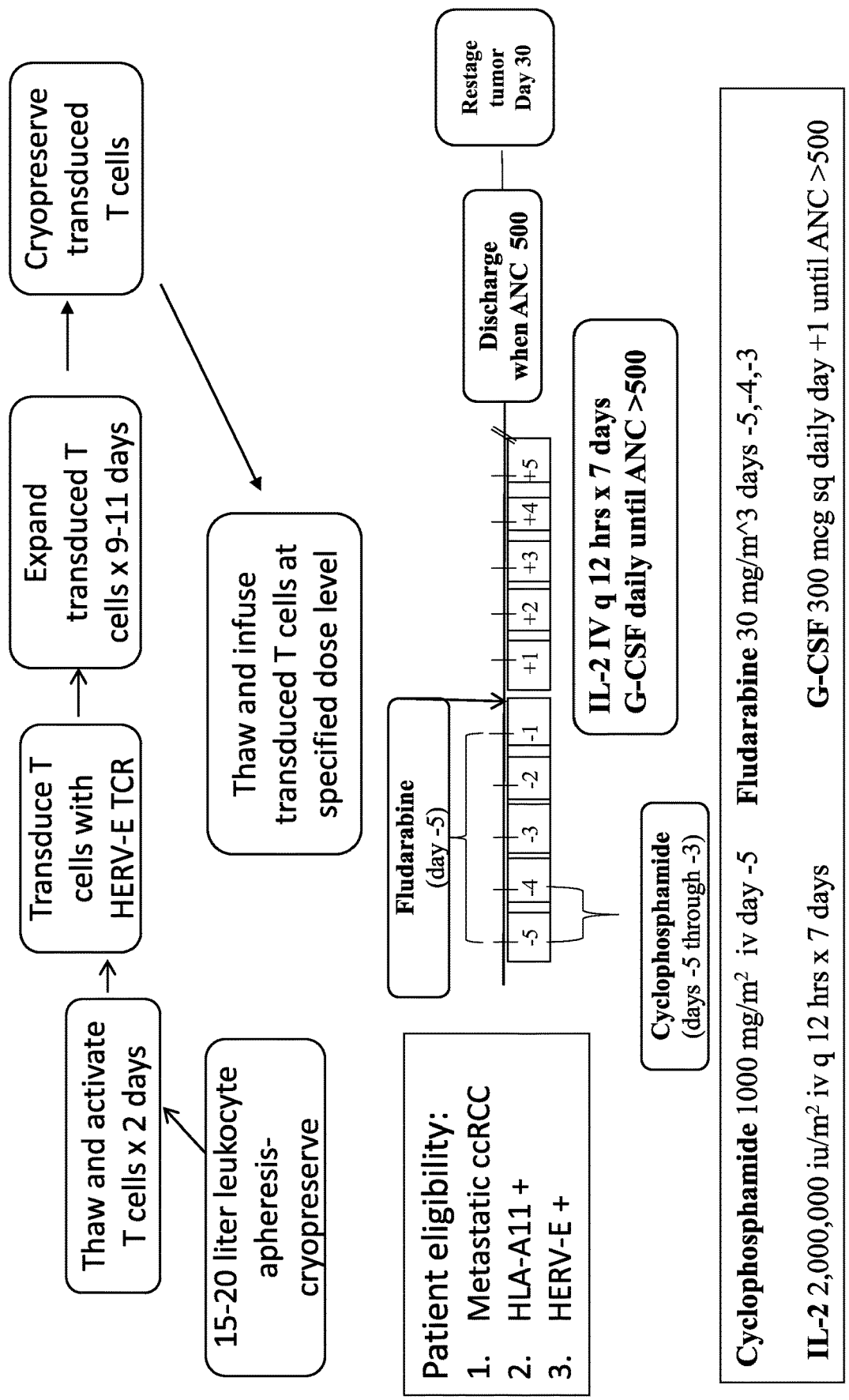
FIG. 9 is a schematic diagram showing an exemplary phase I clinical trial for determining safety and tolerability of HERV-E TCR transduced autologous T cells in HLA-A11 positive patients with advanced ccRCC.

FIG. 9 is a schematic diagram showing an exemplary protocol for determining safety and tolerability of HERV-E TCR transduced T cells (for example prior to clinical implementation).

Subjects with metastatic HERV-E positive ccRCC that is not amenable to complete surgical resection and that is progressive bi-dimensionally evaluable clinically or radiographically and are HLA-A11 positive are selected for this study. Subjects undergo a 15-20 liter leukocyte apheresis to collect (and optionally cryopreserve) $1 \times 10^{10}$ PBMCs. Subsequently, PBMCs ($6 \times 10^8$ to $2 \times 10^9$ cells) are thawed and activated in media containing anti-CD3 (e.g., 50 ng/ml OKT3) and IL-2 (e.g., 300 IU/ml) (and optionally, IL-15, e.g., 100 ng/ml) for 2-3 days followed by depletion for CD4 expressing cells, using immunomagnetic methods. Transduction of about $200 \times 10^6$ T cells with a retrovirus encoding the HLA-A11 restricted HERV-E TCR and CD34t (such as that described in Example 1) is carried out. Following transduction, $0.5-1 \times 10^6$ transduced T cells/kg are enriched using CD34+ immuno-magnetic bead selection and then expanded ex vivo for 9-11 days using irradiated allogeneic PBMC feeder cells (pooled from 3 healthy donors) in IL-2/IL-15 containing media (e.g., 300 IU/ml IL-2 and 100 ng/ml IL-15).

In some embodiments of the protocol, the positive selected CD34+ T cells are placed into a REP to rapidly generate the number of cells needed for infusion. The number of transduced cells that are placed in the REP is determined by the patient's weight and the infusion cohort. To initiate the REP, $1 \times 10^6$ HERV-E TCR transduced cells are combined with $200 \times 10^6$ feeder cells in an upright T175 cm² flask containing 150 ml complete cytokine media (rhIL2/rhIL15) with 30 ng/mL of soluble anti hCD3 antibody (OKT3). The feeder cells consist of PBMC from a minimum of 3 separate normal donors which are mixed together and irradiated with 5000 RAD of irradiation. The flasks are placed upright in a humidified 5% $CO_2$ incubator for 5-6 days. The flasks are removed from the incubator, the cells collected, counted, and re-suspended in fresh media containing 300 IU/mL-IL2 and 100 ng/mL IL15. The cell suspension is transferred into Wave bioreactor bag(s) for further expansion. The culture media is replenished daily with fresh medium containing cytokines by utilizing the Wave bioreactor perfusion system.

Transduced and expanded T cells are cryopreserved at the appropriate dose level (see below) for subsequent infusion into individual subjects following treatment with immune-suppressive chemotherapy.

Three subjects are enrolled sequentially into each of 4 different T cell dose escalating cohorts ($5 \times 10^6$ T cells/kg, $5 \times 10^6$ T cells/kg, $1 \times 10^7$ T cells/kg, or $5 \times 10^7$ T cells/kg). Subjects undergo a non-myeloablative immunosuppressive conditioning regimen with cyclophosphamide 1,000 mg/m² IV (day −5) and fludarabine 30 mg/m² i.v. over 30 minutes daily×3 days (days −5 through −3) followed by infusion of HERV-E TCR transduced T cells on day 0 to deliver the targeted T cell dose. Prior to infusion, T cells undergo a final cell count, and have viability and sterility assessment. Following the T cell infusion, the subject is monitored for up to 4 hours for signs of infusion-related toxicities. Premedication prior to T cell infusion is acetaminophen and i.v. Benadryl. Following the T cell infusion, subjects receive IL-2 i.v. 12 hours at a dose of 2,000,000 IU/m² for 7 days (day 0 through day+6) and G-CSF 300 μg daily from day 1 until neutrophil recovery (ANC>500) occurs. Subjects are discharged from the clinical center following neutrophil recovery and return for weekly visits for 6-8 weeks, where they undergo standard evaluations including physical exams and body weight, and routine clinical labs (hematology and electrolytes). Restaging using PET and CT imaging using RECIST criteria is performed 30 days following the T cell infusion, then every 3 months for the first year, and then every 6 months thereafter until evidence for tumor progression occurs.

The decision to escalate, de-escalate or suspend the dose escalations in the study will follow the rules outlined in Table 2.

TABLE 2

| Outcome: No of DLTs out of No. of Patients at a Given Dose Level | Decision Rule |
| --- | --- |
| 0 DLT out of 3 patients | Enter up to 3 patients at the next dose level |
| 2 DLTs out of 2-3 patients | Stop dose escalation: Enter up to 3 additional patients at the previous dose level if only 3 patients have been treated at that dose. |
| 1 DLT out of 3 patients | Enter up to 3 more patients at the same dose level. |
| 1 DLT out of 6 patients | Enter up to 3 patients at the next dose level |
| 2 DLTs out of 4-6 patients | Stop dose escalation: Enter up to 3 additional patients at the previous dose level if only 3 patients have been treated at that dose. |

Since adverse events associated with adoptive T cell transfer generally occur within 21 days after the T cell infusion, each subject will be observed for 21 days post T cell infusion before the next subject in the cohort or the first subject in the next cohort is treated. Therefore, there will be a minimum of 21 days between the HERV-E TCR transduced T-cells infusion for each patient before the next patient enrolled starts conditioning chemotherapy. Dose-limiting toxicity (DLT) is defined as any adverse event that leads to a discontinuation of the T-cell infusion and/or all grade 3 and 4 toxicities judged probably or definitely associated to the HERV-E TCR transduced CD8+/CD34+ T-cells infusion except for:

Myelosuppression, defined as lymphopenia, neutropenia and thrombocytopenia.

IL-2 expected toxicities. (described section 14.3)

Fludarabine and Cyclophosphamide expected toxicities

Immediate hypersensitivity reactions (excluding symptomatic bronchospasm and grade 4 hypotension) occurring within 2 hours of cell infusion (related to cell infusion) that are reversible to a grade 2 or less within 24 hours of cell administration with standard supportive treatments.

Grade 3 Fever.

Grade 3 autoimmunity, that resolves to less than or equal to a grade 2 autoimmune toxicity within 10 days.

Grade 3 metabolic laboratory abnormalities without significant clinical sequela that resolve to grade 2 within 7 days.

Blood samples are drawn at multiple time points post T cell infusion to assess for circulating HERV-E TCR transduced T cells, which are analyzed by quantitating the percentage and absolute numbers of $CD3^+$ cells expressing CD34. Patients who have tumors which are easily amenable to biopsy may also undergo elective fine needle aspiration of a metastatic tumor lesion to assess for HERV-E TCR transduced T cells using the same methodology as above. Subjects are followed for up to 5 years and are taken off study when disease progression is documented.

Example 6

Treating Renal Cell Carcinoma with HERV-E TCR Transduced T Cells

This example describes methods that can be used to a subject with RCC with HERV-E TCR transduced T cells. However, one skilled in the art will appreciate that methods that deviate from these specific methods can also be used to successfully treat a subject with RCC with HERV-E TCR transduced T cells.

Figure 10:
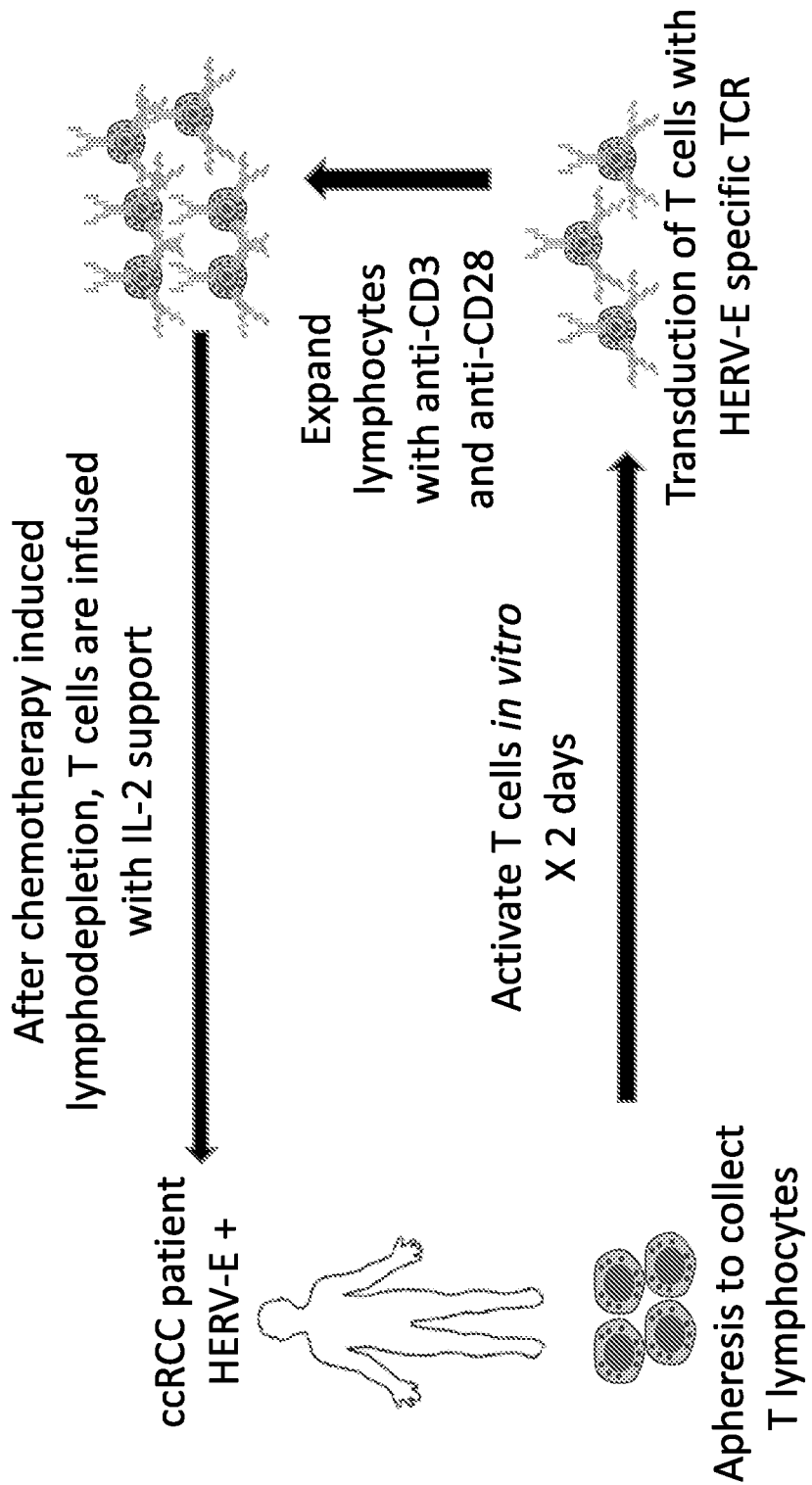
FIG. 10 is a schematic diagram showing an exemplary protocol for treating patients with metastatic ccRCC with HERV-E TCR transduced T cells.

FIG. 10 is a schematic diagram showing an exemplary protocol for treating a subject with RCC.

A subject with RCC (such as metastatic ccRCC) who is HLA-A11 positive and HERV-E positive undergoes apheresis to collect T lymphocytes. T cells are activated with 30 ng/ml anti-CD3 antibody and 300 IU/ml IL-2 in vitro for two days. The T cells are transduced with a retroviral vector including the HERV-E specific TCR described herein (e.g. SEQ ID NO: 6). Lymphocytes are expanded with 30 mg/ml anti-CD3 and 30 ng/ml anti-CD28 for 7-14 days. The subject undergoes chemotherapy induced lymphodepletion (for example, as described in Example 3) and the transduced T cells are infused with IL-2 support at the MTD (for example, determined as described in Example 5).

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A vector comprising the nucleic acid sequence of SEQ ID NO: 6.

2. An isolated host cell comprising the vector of claim 1.

3. The host cell of claim 2, wherein the host cell further comprises a nucleic acid encoding a viral gag protein, a viral pol protein, a viral env protein, or a combination of two or more thereof.

4. The host cell of claim 3, wherein the host cell is a PG13 cell.

5. The host cell of claim 2, wherein the host cell is a lymphocyte.

6. The host cell of claim 5, wherein the lymphocyte is a T cell.

* * * * *